United States Patent
Ohkubo

(10) Patent No.: US 11,193,102 B2
(45) Date of Patent: Dec. 7, 2021

(54) CELL CULTURE APPARATUS

(71) Applicant: Shimadzu Corporation, Kyoto (JP)

(72) Inventor: Tomoki Ohkubo, Kyoto (JP)

(73) Assignee: Shimadzu Corporation, Kyoto (JP)

(*) Notice: Subject to any disclaimer, the term of this patent is extended or adjusted under 35 U.S.C. 154(b) by 95 days.

(21) Appl. No.: 16/433,210

(22) Filed: Jun. 6, 2019

(65) Prior Publication Data

US 2019/0376019 A1   Dec. 12, 2019

(30) Foreign Application Priority Data

Jun. 8, 2018 (JP) .............................. JP2018-110332

(51) Int. Cl.
| | | |
|---|---|---|
| *C12M 1/12* | (2006.01) | |
| *C12M 1/32* | (2006.01) | |
| *C12M 3/00* | (2006.01) | |
| *C12M 1/00* | (2006.01) | |

(52) U.S. Cl.
CPC ............ *C12M 37/04* (2013.01); *C12M 23/12* (2013.01); *C12M 23/26* (2013.01); *C12M 23/48* (2013.01); *C12M 25/16* (2013.01)

(58) Field of Classification Search
CPC ......... B01D 63/10; C12M 3/06; C12M 23/12; C12M 23/16; C12M 23/26; C12M 23/42; C12M 23/48; C12M 25/16; C12M 27/12; C12M 29/00; C12M 37/04
See application file for complete search history.

(56) References Cited

U.S. PATENT DOCUMENTS

| | | | | |
|---|---|---|---|---|
| 3,102,082 A | | 8/1963 | Brewer | |
| 3,853,712 A | | 12/1974 | House et al. | |
| 3,948,732 A | * | 4/1976 | Haddad | ................ C12M 23/24 435/293.2 |
| 5,079,168 A | * | 1/1992 | Amiot | ................... B01D 63/10 435/297.2 |
| 5,154,832 A | * | 10/1992 | Yamamura | .......... B01F 3/04099 210/640 |
| 5,786,215 A | * | 7/1998 | Brown | ................... C12M 23/06 435/297.2 |
| 6,245,557 B1 | * | 6/2001 | Fouts | ..................... C12M 23/08 435/176 |
| 7,273,750 B1 | * | 9/2007 | Olivier | .................. C12M 23/04 220/257.1 |
| 2010/0184629 A1 | * | 7/2010 | Giffin | .................... C12M 23/22 506/33 |

FOREIGN PATENT DOCUMENTS

| | | |
|---|---|---|
| JP | 2009-030010 A | 2/2009 |
| JP | 2012-157244 A | 8/2012 |

* cited by examiner

*Primary Examiner* — Donald R Spamer
*Assistant Examiner* — Lauren A. Ryan
(74) *Attorney, Agent, or Firm* — Muir Patent Law, PLLC

(57) ABSTRACT

A cell culture apparatus includes an introduction-side flow path arranged to allow a culture solution introduced to flow therethrough and be introduced therethrough into each of a plurality of concave wells of a flexible strip circumferentially wound, and a first introduction-side seal provided on an outer circumferential side of the introduction-side flow path, the first introduction-side seal being configured to block flow of the culture solution from the introduction-side flow path to an outer circumferential side of the flexible strip.

19 Claims, 11 Drawing Sheets

FIRST EMBODIMENT

FIRST EMBODIMENT

FIRST EMBODIMENT

FIRST EMBODIMENT

FIRST EMBODIMENT

FIRST EMBODIMENT

SECOND EMBODIMENT

THIRD EMBODIMENT

THIRD EMBODIMENT

THIRD EMBODIMENT

THIRD EMBODIMENT

THIRD EMBODIMENT

THIRD EMBODIMENT

CELL CULTURE APPARATUS

CROSS-REFERENCE TO RELATED APPLICATIONS

This application claims the benefit of priority to Japanese Patent Application No. 2018-110332 filed on Jun. 8, 2018. The entire contents of this application are hereby incorporated herein by reference.

BACKGROUND OF THE INVENTION

Field of the Invention

The present invention relates to a cell culture apparatus, and more particularly, it relates to a cell culture apparatus that cultures cells on the circumferential surface of a circumferentially windable band.

Description of the Background Art

A cell culture apparatus that cultures cells on the circumferential surface of a circumferentially windable band is known in general. Such a cell culture apparatus is disclosed in U.S. Pat. Nos. 3,102,082, 3,853,712, 3,948,732, and 5,786,215, for example.

In a cell culture apparatus disclosed in U.S. Pat. Nos. 3,102,082, 3,853,712, 3,948,732, and 5,786,215, cells are seeded on a surface of a circumferentially windable band. Specifically, the cells adhere to the surface of the band having adhesiveness to the cells such that the cells are seeded. Furthermore, in a state in which the cells are seeded on the surface of the band, a culture solution is introduced to the circumferentially wound band such that the cells are cultured. In addition, a gap having a predetermined size is provided between the bands in a radial direction in order to ensure an interval into which the culture solution flows. The culture solution flows through the gap to portions in which the cells are seeded.

SUMMARY OF THE INVENTION

However, in the cell culture apparatus disclosed in U.S. Pat. Nos. 3,102,082, 3,853,712, 3,948,732, and 5,786,215, the gap having a predetermined size is provided between the bands in the radial direction, and thus there is a disadvantage that the size of the wound band in the radial direction becomes relatively large. On the other hand, when the gap between the bands in the radial direction is relatively small, the culture solution is introduced from one side in a direction in which the central axis of the winding of the band extends such that at least a portion of the culture solution may not flow into the gap and leak to the outer circumferential side of the band. In such a case, a sufficient amount of culture solution is not supplied to the seeded cells, and there is a problem that the cells are not properly cultured.

The present invention has been proposed in order to solve the aforementioned problems, and an object of the present invention is to provide a cell culture apparatus capable of properly culturing cells seeded on a band with a culture solution while significantly reducing or preventing an increase in the size of the wound band in a radial direction.

In order to attain the aforementioned object, a cell culture apparatus according to an aspect of the present invention includes a flexible strip that is circumferentially windable and provided with a plurality of concave wells for culturing cells therein formed on at least one of inner and outer circumferential surfaces of the flexible strip, an introduction-side flow path provided on a first side of the flexible strip in a direction in which a central axis of winding extends in a state in which the flexible strip is circumferentially wound, the introduction-side flow path being arranged to allow a culture solution introduced to flow therethrough and be introduced therethrough into each of the plurality of concave wells of the flexible strip circumferentially wound, and a first introduction-side seal provided on an outer circumferential side of the introduction-side flow path in the state in which the flexible strip is circumferentially wound, the first introduction-side seal being configure to block flow of the culture solution from the introduction-side flow path to an outer circumferential side of the flexible strip.

As described above, the cell culture apparatus according to this aspect of the present invention includes the first introduction-side seal configured to block the flow of the culture solution from the introduction-side flow path to the outer circumferential side of the flexible strip. Accordingly, even when a gap between the flexible strips in a radial direction is relatively small and the culture solution does not flow between the flexible strips but flows toward the outer circumferential side of the flexible strip, the first introduction-side seal can significantly reduce or prevent leakage of the culture solution from the introduction-side flow path to the outer circumferential side of the flexible strip. Consequently, the culture solution, the leakage of which is prevented by the first introduction-side seal, can flow into the gap between the flexible strips. Thus, a sufficient amount of culture solution can be supplied to the cells seeded in the wells. Consequently, the cells seeded on the flexible strip can be properly cultured with the culture solution while an increase in the size of the wound flexible strip in the radial direction is significantly reduced or prevented.

In the aforementioned cell culture apparatus according to this aspect, the flexible strip preferably includes, formed on at least one of the inner circumferential surface and the outer circumferential surface of the flexible strip, a culture solution flow path connected to each of the plurality of concave wells, the culture solution flow path being arranged to allow the culture solution to flow therethrough, and the introduction-side flow path is preferably connected to the culture solution flow path. According to this structure, the culture solution that flows through the introduction-side flow path can easily flow into each of the plurality of wells through the culture solution flow path.

The aforementioned cell culture apparatus according to this aspect preferably further includes an outer circumferential side member connected to the flexible strip and provided on the outer circumferential side of the flexible strip circumferentially wound, and the first introduction-side seal is preferably connected to a portion of the outer circumferential side member on the first side in the direction in which the central axis extends in the state in which the flexible strip is circumferentially wound. According to this structure, unlike the case in which the first introduction-side seal is connected to a portion of the flexible strip on the first side, blocking of the flow of the culture solution into the flexible strip by the first introduction-side seal can be significantly reduced or prevented.

Consequently, the culture solution can be more efficiently introduced into the flexible strip.

In such a case, the outer circumferential side member is preferably flexible and circumferentially windable on the outer circumferential side of the flexible strip, the first introduction-side seal is preferably flexible and integrally provided on the portion of the outer circumferential side member on the first side, and the outer circumferential side member is preferably circumferentially wound around an outer circumference of the flexible strip such that the first introduction-side seal is circumferentially wound on the outer circumferential side of the introduction-side flow path. According to this structure, as compared with the case in which the first introduction-side seal and the outer circumferential side member are provided separately from each other, an increase in the number of components can be significantly reduced or prevented even when the first introduction-side seal is provided.

The aforementioned cell culture apparatus in which the first introduction-side seal is circumferentially wound on the outer circumferential side of the introduction-side flow path preferably further includes a first-side band integrally provided on the first side of the flexible strip in the direction in which the central axis extends, the first-side band having a band shape so as to be circumferentially windable together with the flexible strip, and the introduction-side flow path preferably includes a first-side groove provided between the flexible strip and the first-side band in a state in which the flexible strip and the first-side band are integrally wound, and a plurality of first through-holes that extend from the first-side groove to an outer diameter side of the first-side groove between the flexible strip and the first-side band in the state in which the flexible strip and the first-side band are integrally wound. According to this structure, as compared with the case in which the flexible strip and the first-side band are provided separately from each other, an increase in the number of components can be significantly reduced or prevented. Furthermore, the culture solution introduced through an introduction port can easily flow in the radial direction through the first through-holes that extend in the radial direction.

In the aforementioned cell culture apparatus in which the first introduction-side seal is circumferentially wound on the outer circumferential side of the introduction-side flow path, the culture solution introduced is preferably introduced from an inner circumferential side of the introduction-side flow path into the introduction-side flow path. According to this structure, the first introduction-side seal is provided on the outer circumferential side of the introduction-side flow path, and thus the culture solution can be easily introduced into the introduction-side flow path as compared with the case in which the culture solution is introduced from the outer circumferential side into the introduction-side flow path.

The aforementioned cell culture apparatus in which the first introduction-side seal is circumferentially wound on the outer circumferential side of the introduction-side flow path preferably further includes a first discharge-side flow path provided on a second side of the flexible strip in the direction in which the central axis extends in the state in which the flexible strip is circumferentially wound, the first discharge-side flow path being arranged to allow the culture solution to flow therethrough and be outwardly discharged therethrough, and a first discharge-side seal provided on an outer circumferential side of the first discharge-side flow path in the state in which the flexible strip is circumferentially wound, the first discharge-side seal being configured to block flow of the culture solution from the first discharge-side flow path to the outer circumferential side of the flexible strip, the first discharge-side seal is preferably flexible and integrally provided on the outer circumferential side member, and the outer circumferential side member is preferably circumferentially wound around the outer circumference of the flexible strip such that the first discharge-side seal is circumferentially wound on the outer circumferential side of the first discharge-side flow path. According to this structure, the first discharge-side seal significantly reduces or prevents leakage of the culture solution from the first discharge-side flow path to the outer circumferential side, and thus the culture solution from the first discharge-side flow path can more efficiently flow to a first discharge port. Furthermore, as compared with the case in which the outer circumferential side member and the first discharge-side seal are provided separately from each other, an increase in the number of components can be significantly reduced or prevented even when the first discharge-side seal is provided.

In such a case, the cell culture apparatus preferably further includes a second-side band integrally provided on the second side of the flexible strip in the direction in which the central axis extends, the second-side band having a band shape so as to be circumferentially windable together with the flexible strip, and the first discharge-side flow path preferably includes a second-side groove provided between the flexible strip and the second-side band in a state in which the flexible strip and the second-side band are integrally wound, and a plurality of second through-holes that extend from the second-side groove to an outer diameter side of the second-side groove between the flexible strip and the second-side band in the state in which the flexible strip and the second-side band are integrally wound. According to this structure, as compared with the case in which the flexible strip and the second-side band are provided separately from each other, an increase in the number of components can be significantly reduced or prevented. Moreover, the culture solution of the first discharge-side flow path can easily flow in the radial direction through the plurality of second through-holes that extend in the radial direction.

The aforementioned cell culture apparatus including the first discharge-side flow path preferably further includes an inner circumferential side band connected to the flexible strip, the inner circumferential side band that is circumferentially wound on an inner circumferential side of the flexible strip circumferentially wound, and a first core arranged to allow the flexible strip and the inner circumferential side band to be wound therearound. The inner circumferential side band preferably includes a third through-hole arranged to allow the culture solution introduced to flow therethrough into the introduction-side flow path in a state in which the flexible strip and the inner circumferential side band are wound, and a fourth through-hole arranged to allow the culture solution to flow thereinto from the first discharge-side flow path, and the first core preferably includes a first flow path arranged to allow the culture solution introduced to flow therethrough into the third through-hole of the inner circumferential side band, and a second flow path arranged to allow the culture solution to flow thereinto through the fourth through-hole of the inner circumferential side band. According to this structure, in a state in which the inner circumferential side band is wound, the culture solution can be easily introduced into the introduction-side flow path through the third through-hole of the inner circumferential side band and the first flow path of the first core. Furthermore, the culture solution can be easily discharged from the first discharge-side flow path through the fourth through-hole of the inner circumferential side band and the second flow path of the first core.

In such a case, the cell culture apparatus preferably further includes a first introduction-side protrusion fitted into a first recess provided in the first core on the first side in the direction in which the central axis extends, the first introduction-side protrusion including a third flow path arranged to allow the culture solution introduced to flow therethrough into the first flow path of the first core, and a second introduction-side seal sandwiched between the first introduction-side protrusion and the first core on the first side in the direction in which the central axis extends with respect to a portion arranged to allow the culture solution to flow therethrough from the third flow path into the first flow path. According to this structure, the first introduction-side protrusion including the third flow path is fitted into the first recess, and thus the culture solution can be introduced from the third flow path into the first flow path while the first core is fixed by the first introduction-side protrusion.

In addition, the second introduction-side seal is provided on the first side in the direction in which the central axis extends with respect to the portion arranged to allow the culture solution to flow therethrough from the third flow path into the first flow path such that the second introduction-side seal can significantly reduce or prevent leakage of the culture solution to the first side in the direction in which the central axis extends when the culture solution flows from the third flow path into the first flow path.

The aforementioned cell culture apparatus in which the first core includes the first flow path and the second flow path preferably further includes a first discharge-side protrusion fitted into a second recess provided in the first core on the second side in the direction in which the central axis extends, the first discharge-side protrusion including a fourth flow path arranged to allow the culture solution to flow thereinto from the second flow path of the first core, and a second discharge-side seal sandwiched between the first discharge-side protrusion and the first core on the second side in the direction in which the central axis extends with respect to a portion arranged to allow the culture solution to flow therethrough from the second flow path into the fourth flow path. According to this structure, the first discharge-side protrusion including the fourth flow path is fitted into the second recess, and thus the culture solution from the second flow path can be discharged through the fourth flow path while the first core is fixed by the first discharge-side protrusion.

In addition, the second discharge-side seal is provided on the second side in the direction in which the central axis extends with respect to the portion arranged to allow the culture solution to flow therethrough from the second flow path into the fourth flow path such that the second discharge-side seal can significantly reduce or prevent leakage of the culture solution to the second side in the direction in which the central axis extends when the culture solution flows from the second flow path into the fourth flow path.

In the aforementioned cell culture apparatus including the first discharge-side flow path, the first introduction-side seal corresponding to circumferentially innermost one of a plurality of turns of the first introduction-side seal circumferentially wound on the outer circumferential side of the introduction-side flow path preferably includes a fifth through-hole that overlaps the introduction-side flow path as viewed in a radial direction, and the first discharge-side seal corresponding to circumferentially innermost one of a plurality of turns of the first discharge-side seal circumferentially wound on the outer circumferential side of the first discharge-side flow path preferably includes a sixth through-hole that overlaps the first discharge-side flow path as viewed in the radial direction. According to this structure, air accumulated in the introduction-side flow path and the first discharge-side flow path can be discharged through the fifth through-hole and the sixth through-hole.

The aforementioned cell culture apparatus including the outer circumferential side member preferably further includes an introduction-side housing including an introduction-side main body with a substantially disc shape and a second introduction-side protrusion with a substantially annular shape that protrudes from a surface of the introduction-side main body on a side of the outer circumferential side member toward the outer circumferential side member in the direction in which the central axis extends, the second introduction-side protrusion being provided with the first introduction-side seal at an end on the side of the outer circumferential side member, and the introduction-side flow path is preferably surrounded by the introduction-side main body, the second introduction-side protrusion, the first introduction-side seal, and the wound flexible strip in a state in which the first introduction-side seal provided on the second introduction-side protrusion is in close contact with the outer circumferential side member. According to this structure, in a state in which the first introduction-side seal is in close contact with the outer circumferential side member, the second introduction-side protrusion and the first introduction-side seal can significantly reduce or prevent leakage of the culture solution that flows through the introduction-side flow path to the outer circumferential side. Furthermore, in a state in which the first introduction-side seal is in close contact with the outer circumferential side member, the introduction-side main body can significantly reduce or prevent leakage of the culture solution that flows through the introduction-side flow path from the first side in the direction in which the central axis extends.

In such a case, the cell culture apparatus preferably further includes a second discharge-side flow path provided on a second side of the flexible strip in the direction in which the central axis extends in the state in which the flexible strip is circumferentially wound, the second discharge-side flow path being arranged to allow the culture solution to flow therethrough and be outwardly discharged therethrough, a third discharge-side seal provided on an outer circumferential side with respect to the second discharge-side flow path in the state in which the flexible strip is circumferentially wound, the third discharge-side seal being configured to block the flow of the culture solution from the second discharge-side flow path to the outer circumferential side of the flexible strip, and a discharge-side housing including a discharge-side main body with a substantially disc shape and a second discharge-side protrusion with a substantially annular shape that protrudes from a surface of the discharge-side main body on the side of the outer circumferential side member toward the outer circumferential side member in the direction in which the central axis extends, the second discharge-side protrusion being provided with the third discharge-side seal at the end on the side of the outer circumferential side member. According to this structure, the third discharge-side seal significantly reduces or prevents leakage of the culture solution from the second discharge-side flow path to the outer circumferential side of the flexible strip, and thus the culture solution from the second discharge-side flow path can more efficiently flow to a second discharge port. Furthermore, the third discharge-side seal is provided at the end of the second discharge-side protrusion on the side of the outer circumferential side member, and thus the third discharge-side seal can be easily brought into close contact with the outer circumferential side member.

In the aforementioned cell culture apparatus including the discharge-side housing that includes the discharge-side main body and the second discharge-side protrusion, the second discharge-side flow path is preferably surrounded by the discharge-side main body, the second discharge-side protrusion, the third discharge-side seal, and the wound flexible strip in a state in which the third discharge-side seal provided on the second discharge-side protrusion is in close contact with the outer circumferential side member. According to this structure, in a state in which the third discharge-side seal is in close contact with the outer circumferential side member, the second discharge-side protrusion and the third discharge-side seal can significantly reduce or prevent leakage of the culture solution that flows through the second discharge-side flow path to the outer circumferential side. Furthermore, in a state in which the third discharge-side seal is in close contact with the outer circumferential side member, the discharge-side main body can significantly reduce or prevent leakage of the culture solution that flows through the second discharge-side flow path from the second side in the direction in which the central axis extends.

The aforementioned cell culture apparatus including the introduction-side housing that includes the introduction-side main body and the second introduction-side protrusion preferably further includes a second core arranged to allow the flexible strip to be wound therearound, the second core including a third recess on the first side in the direction in which the central axis extends, and the introduction-side housing preferably includes a third introduction-side protrusion fitted into the third recess of the second core. According to this structure, in a state in which the third discharge-side protrusion is fitted into the third recess of the second core, the culture solution can be introduced to culture the cells. Consequently, the cells can be cultured while the cell culture apparatus is stably fixed.

In the aforementioned cell culture apparatus including the introduction-side housing that includes the introduction-side main body and the second introduction-side protrusion, the culture solution introduced is preferably introduced into the introduction-side flow path from the first side in the direction in which the central axis extends. The introduction-side flow path is provided on the first side of the flexible strip, and thus the culture solution is introduced from the first side of the introduction-side flow path such that the culture solution can be linearly introduced to the flexible strip. Consequently, the structure on the introduction side of the culture solution can be relatively simplified.

The aforementioned cell culture apparatus in which the first core includes the first flow path and the second flow path preferably further includes a housing configured to house the flexible strip and at least a portion of the first core, the housing preferably includes an opening provided in a side surface in the direction in which the central axis extends, and the first core preferably includes a protruding end provided on at least one end side of the first core in the direction in which the central axis extends, the protruding end protruding to an outside of the housing through the opening of the housing. The cell culture apparatus preferably further includes a first tube connected to the first flow path of the protruding end of the first core, the first tube being arranged to allow the culture solution to flow therethrough into the first flow path, a second tube connected to the second flow path of the protruding end of the first core, the second tube being arranged to allow the culture solution to flow thereinto from the second flow path, and an annular sealing member disposed adjacent to the opening of the housing, the annular sealing member circumferentially surrounding the first core. When the first tube and the second tube are inserted into the inside of the housing, the inserted portions of the first tube and the second tube are conceivably fixed by a sealing member, for example, in order to maintain the sealability of the inside of the housing. In such a case, when the first core is rotated in a state in which the first tube and the second tube are inserted into the inside of the housing, the first tube and the second tube may be twisted with the inserted portions of the first tube and the second tube into the housing as fulcrums. On the other hand, when the first tube and the second tube are respectively connected to the first flow path and the second flow path of the protruding end that protrudes to the outside of the housing, it is not necessary to insert the first tube and the second tube into the inside of the housing. Accordingly, when the first core is rotated, twisting of the first tube and the second tube can be significantly reduced or prevented. Furthermore, the annular sealing member is provided adjacent to the opening of the housing such that even when the protruding end of the first core protrudes to the outside of the housing, the sealability of the housing can be maintained by the annular sealing member. Consequently, twisting of the first tube and the second tube can be significantly reduced or prevented while the sealability of the housing is maintained.

In such a case, the housing preferably includes a housing-side protrusion in which the opening is disposed, the housing-side protrusion protruding to the outside of the housing, and the sealing member is preferably sandwiched between an inner circumferential surface of the housing-side protrusion and an outer circumferential surface of the first core inside the housing. According to this structure, the sealing member is sandwiched between the inner circumferential surface of the housing-side protrusion and the outer circumferential surface of the first core such that the sealing member can be stably disposed. Consequently, the first core can be rotated while the sealability of the housing is more effectively maintained by the sealing member.

The aforementioned cell culture apparatus including the first tube and the second tube preferably further includes a pump configured to deliver the culture solution, a reservoir configured to store the culture solution, a third tube including an intermediate portion that connects the pump to the reservoir, a first-side portion that extends from the pump, and a second-side portion that extends from the reservoir, a first joint that separates and connects the first-side portion of the third tube and the first tube, and a second joint that separates and connects the second-side portion of the third tube and the second tube. According to this structure, the first joint and the second joint are provided such that when the first core is rotated, the third tube can be separated from the first tube and the second tube in each of the first joint and the second joint. Consequently, when the first core is rotated, twisting of the first tube and the second tube can be further significantly reduced or prevented.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Embodiments of the present invention are hereinafter described with reference to the drawings.

First Embodiment

The structure of a cell culture apparatus 100 according to a first embodiment is now described with reference to FIGS. 1 to 9.

The cell culture apparatus 100 is used for research in the field of drug discovery and biology, for example, and is expected to be applied to the field of regenerative medicine etc. Specifically, the cell culture apparatus 100 is applied to differentiation induction of pluripotent stem cell-derived tissues for transplantation therapy, expansion of pluripotent stem cells for transplantation therapy, differentiation induction of pluripotent stem cell-derived tissues for drug screening, etc.

(Structure of Cell Culture Apparatus)

Figure 1:
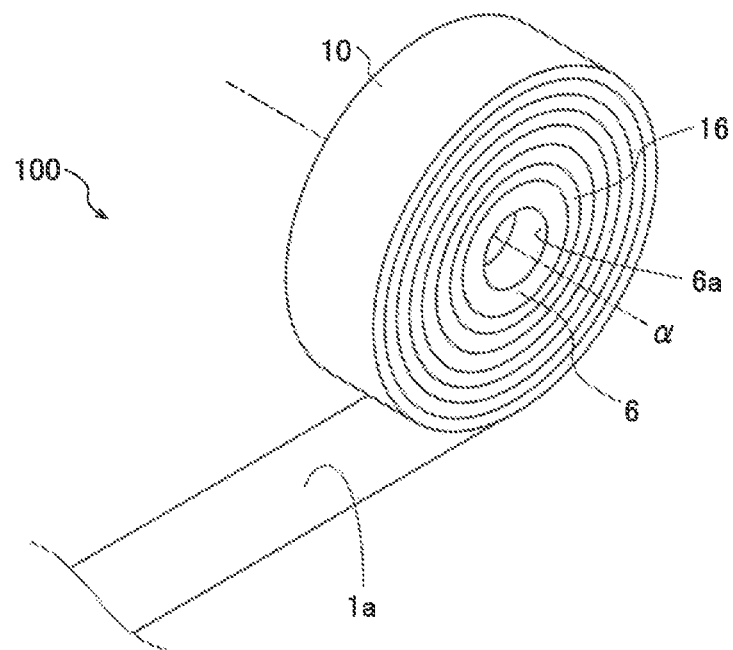
FIG. 1 is a perspective view showing the structure of a (microarray) tape of a cell culture apparatus according to a first embodiment.

As shown in FIG. 1, the cell culture apparatus 100 includes a flexible microarray tape (hereinafter simply referred to as a tape 10) that can be circumferentially wound. The tape 10 has a band shape, and is circumferentially wound in a plurality of layers around a core 6 described below about a central axis α. Although not shown, in the tape 10, a tape main body made of silicone rubber is laminated on a plastic film. In FIG. 1, illustration is omitted except a core 6, the tape 10, and a blank tape 16 described below for simplification. The tape 10 is an example of a "flexible strip" in the claims.

Figure 2:
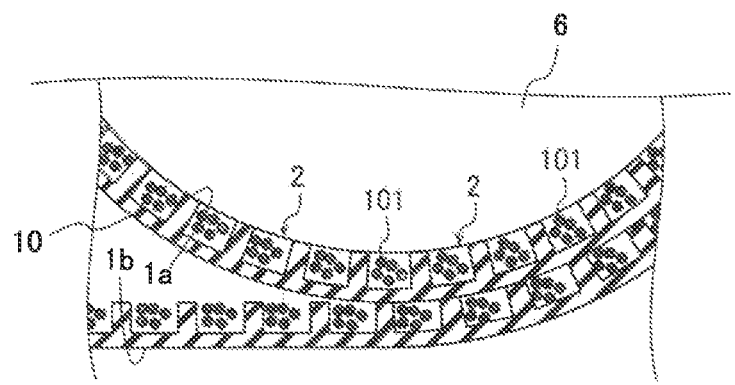
FIG. 2 is an enlarged sectional view showing the structure of the (microarray) tape of the cell culture apparatus according to the first embodiment.

As shown in FIG. 2, on the inner circumferential surface 1a of the tape 10, a plurality of wells 2 in which cells 101 are cultured are provided. The wells 2 are concave, and the cells 101 are contained (seeded) inside the wells 2. The plurality of wells 2 have the same structure (size) as each other. The cells 101 are, for example, induced pluripotent stem (IPS) cells or embryonic stem (ES) cells. In FIG. 2, illustration is omitted except the core 6 and the tape 10 for simplification.

In a state in which the tape 10 is circumferentially wound, the plurality of wells 2 and culture solution flow paths 3 (see FIG. 3) described below are disposed on the inner circumferential side (core 6 side) of the tape 10. The plurality of wells 2 and the culture solution flow paths 3 are covered by the outer circumferential surface 1b of the tape 10 wound on the inner circumferential side of the plurality of wells 2 and the culture solution flow paths 3. An opening 2a (see FIG. 3) of each of the plurality of wells 2 is exposed to the inner circumferential surface 1a. Furthermore, open ends 3a (see FIG. 3) of the culture solution flow paths 3 are exposed to the inner circumferential surface 1a. That is, the outer circumferential surface 1b of the tape 10 wound on the inner circumferential side closes the opening 2a of each of the plurality of wells 2 and the open ends 3a of the culture solution flow paths 3 from the inner circumferential side.

The inner circumferential surface 1a of the tape 10 provided with the plurality of wells 2 is non-adherent to the cells 101. Specifically, the inner circumferential surface 1a of the tape 10 is coated with a non-adherent polymer to the cells 101.

Figure 3:
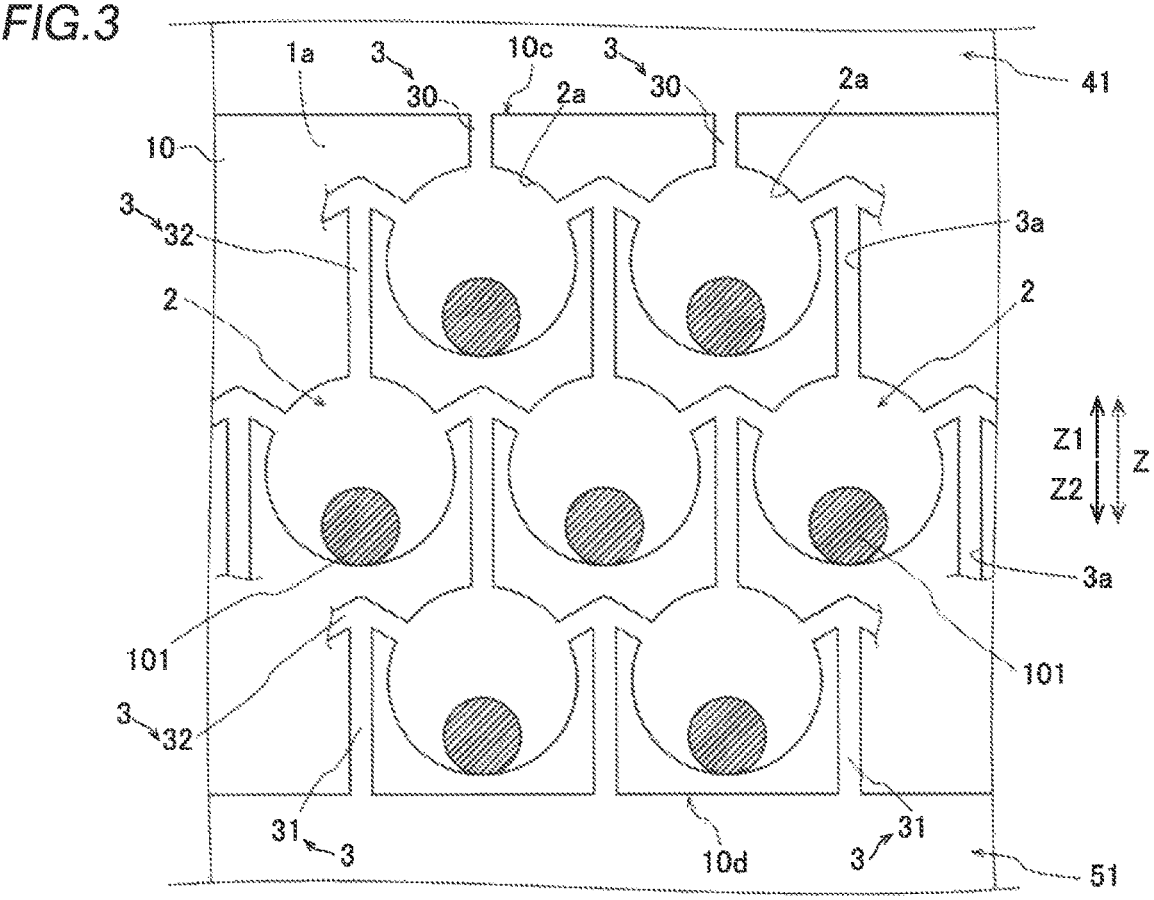
FIG. 3 is a schematic view showing the arrangement relationship between wells and culture solution flow paths in the cell culture apparatus according to the first embodiment.

As shown in FIG. 3, the culture solution flow paths 3 respectively connected to the plurality of wells 2 are provided on the inner circumferential surface 1a of the tape 10. A culture solution flows through the culture solution flow paths 3 such that the culture solution is introduced into each of the plurality of wells 2.

The culture solution flow paths 3 include introduction flow paths 30 that connect an end 10c of the tape 10 on the upper side (Z1 direction side) to a plurality of wells 2 (a plurality of wells 2 disposed in the uppermost stage) disposed in the vicinity of the end 10c. The culture solution flow paths 3 include discharge flow paths 31 that connect an end 10d of the tape 10 on the lower side (Z2 direction side) to a plurality of wells (a plurality of wells 2 disposed in the lowermost stage) disposed in the vicinity of the end 10d. In addition, the culture solution flow paths 3 include connection flow paths 32 that connect a plurality of wells 2 to each other. The plurality of wells 2 are provided in a staggered manner on the inner circumferential surface 1a. Although FIG. 3 illustrates that only three wells 2 are arrayed in a Z direction for simplification, three or more wells 2 are actually arrayed. The term "staggered manner" indicates a state in which wells in adjacent rows are offset from each other in a predetermined direction when a plurality of rows of the wells arrayed along the predetermined direction are disposed side by side so as to be adjacent to each other along a direction orthogonal to the predetermined direction.

Figure 4:
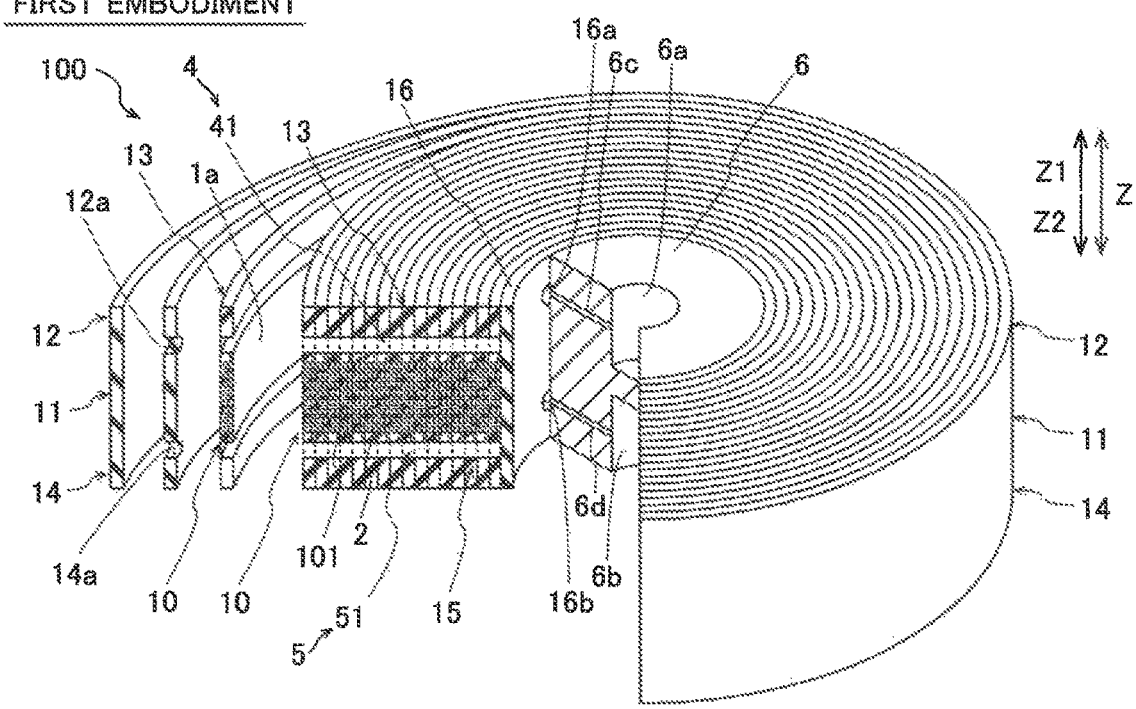
FIG. 4 is a partial sectional view showing the structure of the cell culture apparatus according to the first embodiment.
Figure 5:
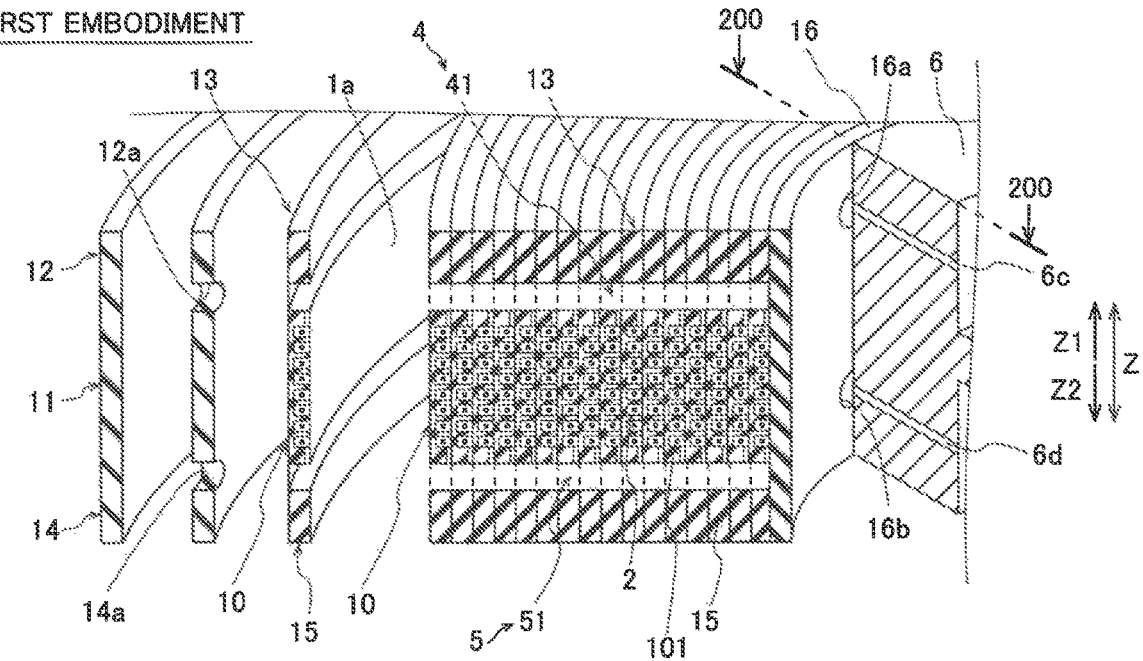
FIG. 5 is an enlarged view of FIG. 4.

As shown in FIGS. 4 and 5, the cell culture apparatus 100 includes an introduction unit 4 that introduces the culture solution. Specifically, the introduction unit 4 includes an introduction port 40 (see FIG. 8) into which the culture solution is introduced from the outside. The introduction port 40 is provided in an upper housing 100a (see FIG. 8). Although not shown, the culture solution is introduced into the introduction port 40 from a pump connected by piping.

The cell culture apparatus 100 includes an introduction-side flow path 41 provided on the first side (Z1 direction side) of the tape 10 in a direction in which the central axis α extends in a state in which the tape 10 is circumferentially wound. The introduction unit 4 includes the introduction-side flow path 41. The culture solution introduced from the outside through the introduction port 40 flows through the introduction-side flow path 41.

In the first embodiment, the introduction-side flow path 41 is connected to the culture solution flow paths 3 (see FIG. 3). Specifically, the introduction-side flow path 41 is directly connected to the introduction flow paths 30 (see FIG. 3).

The cell culture apparatus 100 further includes a blank tape 11 connected to the tape 10. The blank tape 11 is flexible. The blank tape 11 is circumferentially windable on the outer circumferential side of the tape 10 circumferentially wound. Moreover, the concave wells 2 are not provided on the blank tape 11. The blank tape 11 is an example of an "outer circumferential side member" in the claims.

The cell culture apparatus 100 includes a tape-like seal 12 provided on the outer circumferential side of the introduction-side flow path 41 in a state in which the tape 10 is circumferentially wound. The tape-like seal 12 is flexible and windable. The tape-like seal 12 blocks the flow of the culture solution from the introduction-side flow path 41 to the outer circumferential side of the tape 10. The culture solution is introduced into each of the plurality of wells 2 of the tape 10 circumferentially wound through the introduction-side flow path 41. The tape-like seal 12 is an example of a "first introduction-side seal" in the claims.

Figure 6:
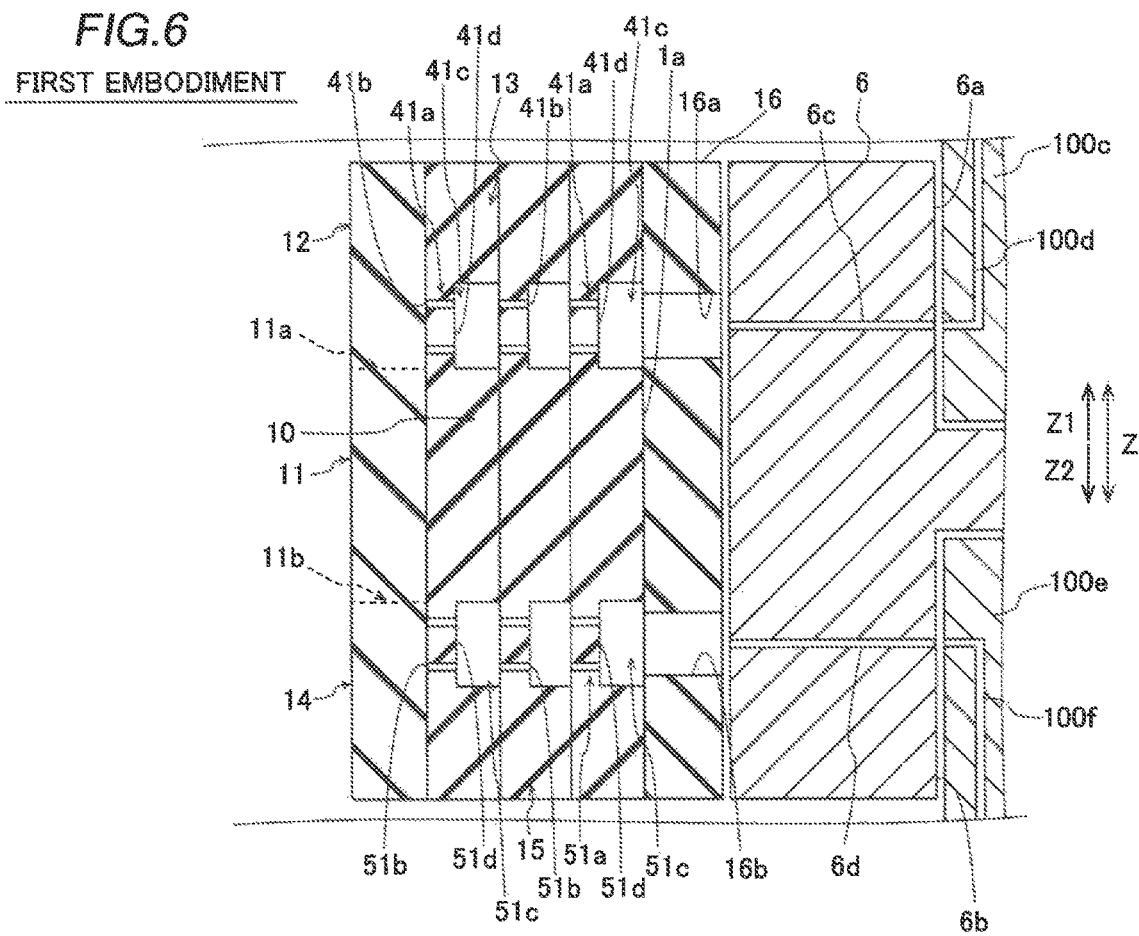
FIG. 6 is a schematic sectional view taken along the line 200-200 in FIG. 5.

Specifically, the tape-like seal 12 is connected to a portion 11a (see FIG. 6) of the blank tape 11 on the first side in the direction in which the central axis α extends in a state in which the tape 10 and the blank tape 11 are circumferentially wound. The portion 11a is an end of the blank tape 11 on the first side (Z1 direction side). The portion 11a is provided at a height substantially equal to that of a boundary (end 10c; see FIG. 3) between the tape 10 and the introduction-side flow path 41 in the Z direction. In FIG. 6, the number of turns of the tape 10 and the number of turns of the blank tape 11 are reduced for simplification.

More specifically, the tape-like seal 12 is integrally provided on the portion 11a of the blank tape 11 on the first side. That is, the tape-like seal 12 and the blank tape 11 are wound integrally. The blank tape 11 is circumferentially wound around the outer circumference of the tape 10 such that the tape-like seal 12 is circumferentially wound on the outer circumferential side of the introduction-side flow path 41. In addition, the tape-like seal 12 is circumferentially wound also on the outer circumferential side of a blank tape 13 described below.

The cell culture apparatus 100 further includes the blank tape 13 integrally provided on the first side (Z1 direction side) of the tape 10 in the direction in which the central axis α extends. The blank tape 13 has a band shape so as to be circumferentially windable together with the tape 10. The concave wells 2 are not provided on the blank tape 13. The blank tape 13 is an example of a "first-side band" in the claims.

The introduction-side flow path 41 is provided between the tape 10 and the blank tape 13. Specifically, the introduction-side flow path 41 is sandwiched between the tape 10 and the blank tape 13 in the Z direction.

The cell culture apparatus 100 includes a discharge unit 5 that discharges the culture solution. Specifically, the discharge unit 5 includes a discharge port 50 (see FIG. 8) through which the culture solution is outwardly discharged. The discharge port 50 is provided in a lower housing 100b (see FIG. 8). The culture solution discharged through the discharge port 50 is discharged by a pump (not shown) connected to the discharge port 50 through piping (not shown).

The cell culture apparatus 100 includes a discharge-side flow path 51 provided on the second side (Z2 direction side) of the tape 10 in the direction in which the central axis α extends in a state in which the tape 10 is circumferentially wound. The discharge unit 5 includes the discharge-side flow path 51. The culture solution to be outwardly discharged through the discharge port 50 flows through the discharge-side flow path 51. The discharge-side flow path 51 is an example of a "first discharge-side flow path" in the claims.

The discharge-side flow path 51 is connected to the culture solution flow paths 3 (see FIG. 3). Specifically, the discharge-side flow path 51 is directly connected to the discharge flow paths 31 (see FIG. 3). Thus, the culture solution that has flowed into the culture solution flow paths 3 from the introduction-side flow path 41 flows into the discharge-side flow path 51 through the culture solution flow paths 3.

The cell culture apparatus 100 includes a tape-like seal 14 provided on the outer circumferential side of the discharge-side flow path 51 in a state in which the tape 10 is circumferentially wound. The tape-like seal 14 is flexible and windable. The tape-like seal 14 blocks the flow of the culture solution from the discharge-side flow path 51 to the outer circumferential side of the tape 10. The tape-like seal 14 is an example of a "first discharge-side seal" in the claims.

Specifically, the tape-like seal 14 is connected to a portion 11b (see FIG. 6) of the blank tape 11 on the second side in the direction in which the central axis α extends in a state in which the tape 10 and the blank tape 11 are circumferentially wound. The portion 11b is an end of the blank tape 11 on the second side (Z2 direction side). The portion 11b is provided at a height substantially equal to a boundary (end 10d; see FIG. 3) between the tape 10 and the discharge-side flow path 51 in the Z direction.

More specifically, the tape-like seal 14 is integrally provided on the portion 11b of the blank tape 11 on the second side. That is, the tape-like seal 14 and the blank tape 11 are wound integrally. The blank tape 11 is circumferentially wound around the outer circumference of the tape 10 such that the tape-like seal 14 is circumferentially wound on the outer circumferential side of the discharge-side flow path 51. In addition, the tape-like seal 14 is circumferentially wound also on the outer circumferential side of a blank tape 15 described below.

The cell culture apparatus 100 further includes the blank tape 15 integrally provided on the second side (Z2 direction side) of the tape 10 in the direction in which the central axis α extends. The blank tape 15 has a band shape so as to be circumferentially windable together with the tape 10. The concave wells 2 are not provided on the blank tape 15. The blank tape 15 is an example of a "second-side band" in the claims.

The discharge-side flow path 51 is provided between the tape 10 and the blank tape 15. Specifically, the discharge-side flow path 51 is sandwiched between the tape 10 and the blank tape 15 in the Z direction.

As shown in FIGS. 4 and 5, each of the introduction-side flow path 41 and the discharge-side flow path 51 extends in the radial direction on the cross-section in the radial direction. That is, the introduction-side flow path 41 and the discharge-side flow path 51 are substantially parallel to each other.

In the first embodiment, as shown in FIG. 6, the introduction-side flow path 41 (see FIGS. 4 and 5) has a groove shape that connects the tape 10 to the blank tape 13 by a bottom 41a. Specifically, the introduction-side flow path 41 includes a plurality of through-holes 41b and a groove 41c. The groove 41c is provided between the tape 10 and the blank tape 13 in a state in which the tape 10 and the blank tape 13 are integrally wound. Furthermore, the plurality of through-holes 41b extend outward from the groove 41c between the tape 10 and the blank tape 13. The bottom 41a indicates a portion of the groove 41c on the outer diameter side (outer surface side) in the blank tape 13. The groove 41c is connected to the through-holes 41b. More specifically, the through-holes 41b are connected to the circumferential surface 41d of the groove 41c on the outer circumferential side. The through-holes 41b and the groove 41c are examples of a "first through-hole" and a "first-side groove" in the claims, respectively.

The through-holes 41b extend to the outer diameter side from the groove 41c (circumferential surface 41d) to which the through-holes 41b are connected. The through-holes 41b that extend to the outer diameter side from the connected groove 41c (circumferential surface 41d) are connected to the groove 41c provided on the outer diameter side. Thus, the culture solution that flows through the groove 41c flows to the outer diameter side through the through-holes 41b, and flows into the groove 41c provided on the outer diameter side.

Consequently, the culture solution introduced through the introduction port 40 flows through the introduction-side flow path 41 from the inner circumferential side toward the outer circumferential side. That is, the culture solution flows from the inner circumferential side of the cell culture apparatus 100 to the outer circumferential side thereof through the groove 41c and the through-holes 41b arrayed in the radial direction due to the tape 10 and the blank tape 13 circumferentially wound.

In the first embodiment, the discharge-side flow path 51 has a groove shape that connects the tape 10 to the blank tape 15 by a bottom 51a. Specifically, the discharge-side flow path 51 includes a plurality of through-holes 51b and a groove 51c. The groove 51c is provided between the tape 10 and the blank tape 15 in a state in which the tape 10 and the blank tape 15 are integrally wound. Furthermore, the plurality of through-holes 51b extend to the outer diameter side from the groove 51c between the tape 10 and the blank tape 15. The bottom 51a indicates a portion of the groove 51c on the outer diameter side (outer surface side) in the blank tape 15. The groove 51c is connected to the through-holes 51b. More specifically, the through-holes 51b are connected to the circumferential surface 51d of the groove 51c on the outer circumferential side. The through-holes 51b and the groove 51c are examples of a "second through-hole" and a "second-side groove" in the claims, respectively.

The through-holes 51b extend to the outer diameter side from the groove 51c (circumferential surface 51d) to which the through-holes 51b are connected. The through-holes 51b that extend to the outer diameter side from the connected groove 51c (circumferential surface 51d) are connected to the groove 51c provided on the outer diameter side. Thus, the culture solution that flows through the groove 51c flows into the groove 51c on the inner diameter side through the through-holes 51b on the inner diameter side.

Consequently, the culture solution that has flowed into the discharge-side flow path 51 from the culture solution flow paths 3 (see FIG. 3) flows through the discharge-side flow path 51 from the outer circumferential side toward the inner circumferential side. That is, the culture solution flows from the outer circumferential side of the cell culture apparatus 100 to the inner circumferential side thereof through the groove 51c and the through-holes 51b arrayed in the radial direction due to the tape 10 and the blank tape 15 circumferentially wound.

The through-holes 41b are provided substantially equally (see FIG. 7) in a circumferential direction in the circumferential surface 41d. Furthermore, the through-holes 51b are provided substantially equally (see FIG. 7) in the circumferential direction in the circumferential surface 51d. Although FIGS. 6 and 7 illustrate that two through-holes 41b and two through-holes 51b are arrayed in the Z direction, the number of through-holes is not limited to two.

Figure 7:
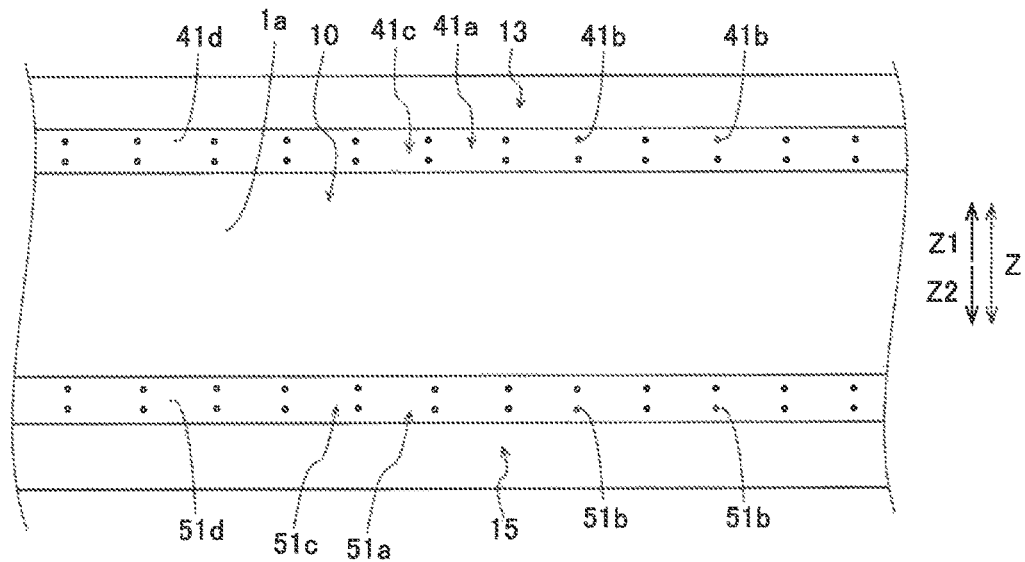
FIG. 7 is a diagram showing a groove of the cell culture apparatus according to the first embodiment, as viewed in a radial direction.

The groove 41c and the groove 51c extend substantially parallel to each other (see FIG. 7).

The cell culture apparatus 100 further includes a blank tape 16 connected to the tape 10. The blank tape 16 is flexible and circumferentially wound on the inner circumferential side of the tape 10 circumferentially wound. The blank tape 16 is not provided with the concave wells 2 on the circumferential surface. The blank tape 16 is an example of an "inner circumferential side band" in the claims.

The cell culture apparatus 100 further includes the core 6 around which the tape 10, the blank tape 11, and the blank tape 16 are wound. The core 6 includes a recess 6a on the first side (Z1 direction side) in the direction in which the central axis α (see FIG. 1) extends. In addition, the core 6 includes a recess 6b on the second side (Z2 direction side) in the direction in which the central axis α extends. Each of the core 6, the recess 6a, and the recess 6b has a substantially cylindrical shape. The recess 6a and the recess 6b are provided substantially at the center of the core 6 as viewed from the Z1 (Z2) direction side. The core 6 is an example of a "first core" in the claims. The recess 6a and the recess 6b are examples of a "first recess" and a "second recess" in the claims, respectively.

In the first embodiment, the blank tape 16 includes a through-hole 16a through which the culture solution introduced through the introduction port 40 (see FIG. 8) flows into the introduction-side flow path 41 (see FIG. 5) in a state in which the tape 10 and the blank tape 16 are wound, and a through-hole 16b into which the culture solution flows from the discharge-side flow path 51 (see FIG. 5) in a state in which the tape 10 and the blank tape 16 are wound. Specifically, the through-hole 16a extends in the radial direction so as to connect the groove 41c provided in the circumferentially innermost tape 10 to a flow path 6c described below. The through-hole 16b extends in the radial direction so as to connect the groove 51c provided in the circumferentially innermost tape 10 to a flow path 6d described below. The through-hole 16a and the through-hole 16b are examples of a "third through-hole" and a "fourth through-hole" in the claims, respectively.

Although it is illustrated that the blank tape 16 is wound in only one layer, the blank tape 16 may be wound in a plurality of layers. In such a case, the through-hole 16a and the through-hole 16b are provided in all the layers of the blank tape 16, the through-holes 16a overlap each other, and the through-holes 16b overlap each other, as viewed in the radial direction.

The culture solution introduced through the introduction port 40 is introduced from the inner circumferential side into the introduction-side flow path 41. That is, the culture solution flows into the introduction-side flow path 41 through the through-hole 16a provided on the inner circumferential side of the introduction-side flow path 41. The culture solution of the discharge-side flow path 51 flows into the flow path 6d described below through the through-hole 16b provided on the inner circumferential side of the discharge-side flow path 51.

The core 6 includes the flow path 6c through which the culture solution introduced through the introduction port 40 flows into the through-hole 16a of the blank tape 16, and the flow path 6d into which the culture solution flows through the through-hole 16b of the blank tape 16. Specifically, the flow path 6c extends in the radial direction so as to connect the through-hole 16a to a flow path 100d described below. The flow path 6d extends in the radial direction so as to connect the through-hole 16b to a flow path 100f described below. That is, the flow path 6c and the flow path 6d extend substantially parallel to each other. The flow path 6c and the flow path 6d are examples of a "first flow path" and a "second flow path" in the claims, respectively.

Figure 8:
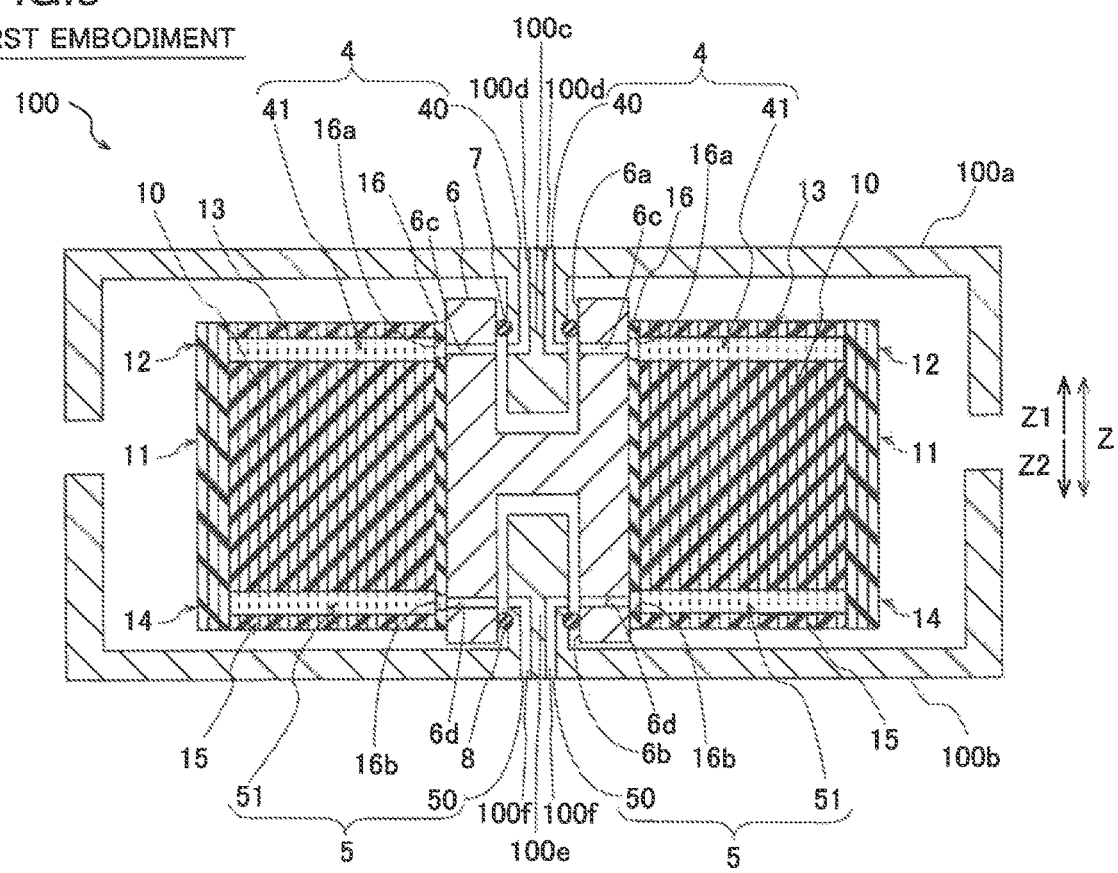
FIG. 8 is a sectional view illustrating the overall structure of the cell culture apparatus according to the first embodiment.

In the first embodiment, as shown in FIG. 8, the cell culture apparatus 100 includes a protrusion 100c fitted into the recess 6a of the core 6. The protrusion 100c is integrally provided on the upper housing 100a. The protrusion 100c has a substantially cylindrical shape. The protrusion 100c is an example of a "first introduction-side protrusion" in the claims.

The protrusion 100c includes the flow path 100d through which the culture solution introduced through the introduction port 40 flows into the flow path 6c of the core 6. Specifically, the introduction port 40 is provided at one end of the flow path 100d. In other words, the introduction port 40 is an inlet of the flow path 100d. The flow path 100d extends in a substantially L shape so as to pass through the upper housing 100a (protrusion 100c) between the introduction port 40 of the upper housing 100a and the flow path 6c. The flow path 100d is an example of a "third flow path" in the claims.

The cell culture apparatus 100 includes a protrusion 100e fitted into the recess 6b of the core 6. The protrusion 100e is integrally provided on the lower housing 100b. The protrusion 100e has a substantially cylindrical shape. The protrusion 100e is an example of a "first discharge-side protrusion" in the claims.

The protrusion 100e includes a flow path 100f into which the culture solution flows from the flow path 6d of the core 6. Specifically, the discharge port 50 is provided at one end of the protrusion 100e. In other words, the discharge port 50 is an outlet of the flow path 100f. The flow path 100f extends in a substantially L shape so as to pass through the lower housing 100b (protrusion 100e) between the discharge port 50 of the lower housing 100b and the flow path 6d. The flow path 100f is an example of a "fourth flow path" in the claims.

The introduction-side flow path 41 and the discharge-side flow path 51 are configured as described above such that it is not necessary to directly connect a surrounding member (such as a pump that supplies the culture solution) to the tape 10 in order to introduce and discharge the culture solution. Thus, the operation such as winding (unwinding) of the tape 10 can be facilitated.

The cell culture apparatus 100 includes a gasket 7 sandwiched between the protrusion 100c and the core 6 on the first side (Z1 direction side) in the direction in which the central axis α extends with respect to a portion in which the culture solution flows from the flow path 100d into the flow path 6c. Specifically, the gasket 7 has an annular shape, and the cylindrical protrusion 100c is fitted into an opening of the gasket 7. The gasket 7 is an example of a "second introduction-side seal" in the claims.

The cell culture apparatus 100 includes a gasket 8 sandwiched between the protrusion 100e and the core 6 on the second side (Z2 direction side) in the direction in which the central axis α extends with respect to a portion in which the culture solution flows from the flow path 6d into the flow path 100f. Specifically, the gasket 8 has an annular shape, and the cylindrical protrusion 100e is fitted into an opening of the gasket 8. The gasket 8 is an example of a "second discharge-side seal" in the claims.

Two flow paths 6c, two flow paths 6d, two flow paths 100d, and two flow paths 100f are bilaterally symmetrical with respect to the central axis α. Furthermore, two introduction ports 40, two discharge ports 50, two through-holes 16a, and two through-holes 16b are bilaterally symmetrical with respect to the central axis α.

Figure 9:
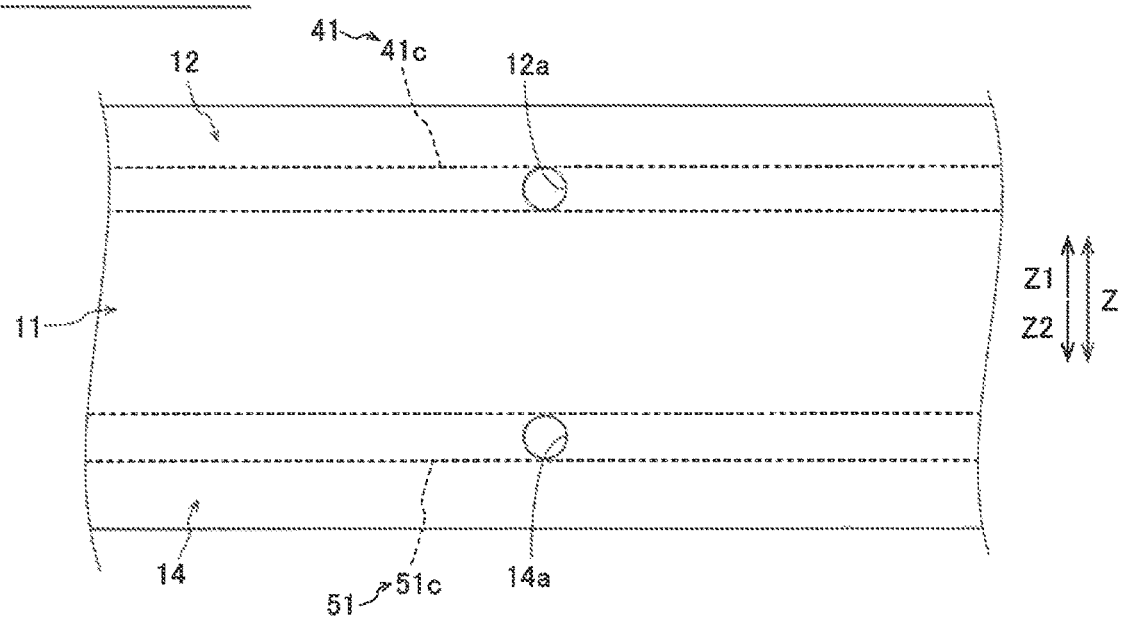
FIG. 9 is a diagram showing a blank tape on the outer circumferential side of the cell culture apparatus according to the first embodiment, as viewed in the radial direction.

As shown in FIG. 9, a through-hole 12a is provided in the tape-like seal 12 corresponding to the circumferentially innermost one of a plurality of turns. Furthermore, a through-hole 14a is provided in the circumferentially innermost tape-like seal 14 (which is wound directly on the tape 10). The through-hole 12a is provided at a position that overlaps the introduction-side flow path 41 (groove 41c) as viewed in the radial direction. The through-hole 14a is provided at a position that overlaps the discharge-side flow path 51 (groove 51c) as viewed in the radial direction. Thus, the tape-like seal 12 and the tape-like seal 14 are wound and then the culture solution is flowed such that air accumulated in the introduction-side flow path 41 and the discharge-side flow path 51 can be discharged through each of the through-hole 12a and the through-hole 14a. The through-hole 12a and the through-hole 14a are examples of a "fifth through-hole" and a "sixth through-hole" in the claims, respectively.

The tape-like seal 12 in which the through-hole 12a is provided (the tape-like seal 14 in which the through-hole 14a is provided) is wound on the circumferentially innermost one of a plurality of turns. Note that a plurality of (two, for example) through-holes 12a and a plurality of (two, for example) through-holes 14a may be provided in the circumferential direction.

Advantages Derived from First Embodiment

According to the first embodiment, the following advantages are obtained.

According to the first embodiment, as described above, the cell culture apparatus 100 includes the introduction port 40 into which the culture solution is introduced from the outside, and the introduction-side flow path 41 provided on the first side of the tape 10 in the direction in which the central axis α of the winding extends in a state in which the tape 10 is circumferential wound and through which the culture solution introduced from the outside flows and the introduced culture solution is introduced into each of the plurality of wells 2 of the tape 10 circumferentially wound. Furthermore, the cell culture apparatus 100 includes the tape-like seal 12 provided on the outer circumferential side of the introduction-side flow path 41 in a state in which the tape 10 is circumferentially wound and that blocks the flow of the culture solution from the introduction-side flow path 41 to the outer circumferential side of the tape 10. Accordingly, even when the gap between the tapes 10 in the radial direction is relatively small and the culture solution does not flow between the tapes 10 but flows toward the outer circumferential side of the tape 10, the tape-like seal 12 can significantly reduce or prevent leakage of the culture solution from the introduction-side flow path 41 to the outer circumferential side of the tape 10. Consequently, the culture solution, the leakage of which is prevented by the tape-like seal 12, can flow into the gap between the tapes 10. Thus, a sufficient amount of culture solution can be supplied to the cells 101 seeded in the wells 2. Consequently, the cells 101 seeded on the tape 10 can be properly cultured with the culture solution while an increase in the size of the wound tape 10 in the radial direction is significantly reduced or prevented.

According to the first embodiment, as described above, in the cell culture apparatus 100, the introduction-side flow path 41 is connected to the culture solution flow paths 3. Accordingly, the culture solution that flows through the introduction-side flow path 41 can easily flow into each of the plurality of wells 2 through the culture solution flow paths 3.

According to the first embodiment, as described above, in the cell culture apparatus 100, the tape-like seal 12 is connected to the portion 11$a$ of the blank tape 11 on the first side in the direction in which the central axis $\alpha$ extends in a state in which the tape 10 and the blank tape 11 are circumferentially wound. Accordingly, unlike the case in which the tape-like seal 12 is connected to a portion of the tape 10 on the first side, blocking of the flow of the culture solution into the tape 10 by the tape-like seal 12 can be significantly reduced or prevented. Consequently, the culture solution can be more efficiently introduced into the tape 10.

According to the first embodiment, as described above, in the cell culture apparatus 100, the tape-like seal 12 is flexible and integrally provided on the portion 11$a$ of the blank tape 11 on the first side, and the blank tape 11 is circumferentially wound around the outer circumference of the tape 10 such that the tape-like seal 12 is circumferentially wound on the outer circumferential side of the introduction-side flow path 41. Accordingly, as compared with the case in which the tape-like seal 12 and the blank tape 11 are provided separately from each other, an increase in the number of components can be significantly reduced or prevented even when the tape-like seal 12 is provided.

According to the first embodiment, as described above, the cell culture apparatus 100 includes the blank tape 13 integrally provided on the first side of the tape 10 in the direction in which the central axis $\alpha$ extends and having a band shape so as to be circumferentially windable together with the tape 10. Furthermore, in the cell culture apparatus 100, the introduction-side flow path 41 includes the groove 41$c$ provided between the tape 10 and the blank tape 13 in a state in which the tape 10 and the blank tape 13 are integrally wound, and the plurality of through-holes 41$b$ that extend from the groove 41$c$ to the outer diameter side of the groove 41$c$ between the tape 10 and the blank tape 13 in a state in which the tape 10 and the blank tape 13 are integrally wound. Accordingly, as compared with the case in which the tape 10 and the blank tape 13 are provided separately from each other, an increase in the number of components can be significantly reduced or prevented. Furthermore, the culture solution introduced through the introduction port 40 can easily flow in the radial direction through the through-holes 41$b$ that extend in the radial direction.

According to the first embodiment, as described above, in the cell culture apparatus 100, the culture solution introduced through the introduction port 40 is introduced from the inner circumferential side into the introduction-side flow path 41. Accordingly, the tape-like seal 12 is provided on the outer circumferential side of the introduction-side flow path 41, and thus the culture solution can be easily introduced into the introduction-side flow path 41 as compared with the case in which the culture solution is introduced from the outer circumferential side into the introduction-side flow path 41.

According to the first embodiment, as described above, the cell culture apparatus 100 includes the discharge unit 5 including the discharge-side flow path 51 provided on the second side of the tape 10 in the direction in which the central axis $\alpha$ extends in a state in which the tape 10 is circumferentially wound and the discharge port 50 into which the culture solution flows from the discharge-side flow path 51 and through which the culture solution is outwardly discharged. Furthermore, the cell culture apparatus 100 includes the tape-like seal 14 provided on the outer circumferential side of the discharge-side flow path 51 in a state in which the tape 10 is circumferentially wound, and that blocks the flow of the culture solution from the discharge-side flow path 51 to the outer circumferential side of the tape 10. In addition, in the cell culture apparatus 100, the tape-like seal 14 is flexible and integrally provided on the blank tape 11, and the blank tape 11 is circumferentially wound around the outer circumference of the tape 10 such that the tape-like seal 14 is circumferentially wound on the outer circumferential side of the discharge-side flow path 51. Accordingly, the tape-like seal 14 significantly reduces or prevents leakage of the culture solution from the discharge-side flow path 51 to the outer circumferential side, and thus the culture solution from the discharge-side flow path 51 can more efficiently flow to the discharge port 50. Furthermore, as compared with the case in which the blank tape 11 and the tape-like seal 14 are provided separately from each other, an increase in the number of components can be significantly reduced or prevented even when the tape-like seal 14 is provided.

According to the first embodiment, as described above, the cell culture apparatus 100 includes the blank tape 15 integrally provided on the second side of the tape 10 in the direction in which the central axis $\alpha$ extends, and having a band shape so as to be circumferentially windable together with the tape 10. Furthermore, in the cell culture apparatus 100, the discharge-side flow path 51 includes the groove 51$c$ provided between the tape 10 and the blank tape 15 in a state in which the tape 10 and the blank tape 15 are integrally wound, and the plurality of through-holes 51$b$ that extend from the groove 51$c$ to the outer diameter side of the groove 51$c$ between the tape 10 and the blank tape 15 in a state in which the tape 10 and the blank tape 15 are integrally wound. Accordingly, as compared with the case in which the tape 10 and the blank tape 15 are provided separately from each other, an increase in the number of components can be significantly reduced or prevented. Moreover, the culture solution of the discharge-side flow path 51 can easily flow in the radial direction through the plurality of through-holes 51$b$ that extend in the radial direction.

According to the first embodiment, as described above, in the cell culture apparatus 100, the core 6 includes the flow path 6$c$ through which the culture solution introduced through the introduction port 40 flows into the through-hole 16$a$ of the blank tape 16, and the flow path 6$d$ into which the culture solution flows through the through-hole 16$b$ of the blank tape 16. Accordingly, in a state in which the blank tape 16 is wound, the culture solution can be easily introduced into the introduction-side flow path 41 through the through-hole 16a of the blank tape 16 and the flow path 6c of the core 6. Furthermore, the culture solution can be easily discharged from the discharge-side flow path 51 through the through-hole 16b of the blank tape 16 and the flow path 6d of the core 6.

According to the first embodiment, as described above, the cell culture apparatus 100 includes the protrusion 100c fitted into the recess 6a provided in the core 6 on the first side in the direction in which the central axis α extends. Furthermore, the protrusion 100c includes the flow path 100d through which the culture solution introduced through the introduction port 40 flows into the flow path 6c of the core 6. In addition, the cell culture apparatus 100 includes the gasket 7 sandwiched between the protrusion 100c and the core 6 on the first side in the direction in which the central axis α extends with respect to the portion in which the culture solution flows from the flow path 100d into the flow path 6c. Accordingly, the protrusion 100c including the flow path 100d is fitted into the recess 6a, and thus the culture solution can be introduced from the flow path 100d into the flow path 6c while the core 6 is fixed by the protrusion 100c.

In addition, the gasket 7 is provided on the first side in the direction in which the central axis α extends with respect to the portion in which the culture solution flows from the flow path 100d into the flow path 6c such that the gasket 7 can significantly reduce or prevent leakage of the culture solution to the first side in the direction in which the central axis α extends when the culture solution flows from the flow path 100d into the flow path 6c.

According to the first embodiment, as described above, the cell culture apparatus 100 includes the protrusion 100e fitted into the recess 6b provided in the core 6 on the second side in the direction in which the central axis α extends. Furthermore, the protrusion 100e includes the flow path 100f into which the culture solution flows from the flow path 6d of the core 6. In addition, the cell culture apparatus 100 includes the gasket 8 sandwiched between the protrusion 100e and the core 6 on the second side in the direction in which the central axis α extends with respect to the portion in which the culture solution flows from the flow path 6d into the flow path 100f. Accordingly, the protrusion 100e including the flow path 100f is fitted into the recess 6b, and thus the culture solution from the flow path 6d can be discharged through the flow path 100f while the core 6 is fixed by the protrusion 100e.

In addition, the gasket 8 is provided on the second side in the direction in which the central axis α extends with respect to the portion in which the culture solution flows from the flow path 6d into the flow path 100f such that the gasket 8 can significantly reduce or prevent leakage of the culture solution to the second side in the direction in which the central axis α extends when the culture solution flows from the flow path 6d into the flow path 100f.

According to the first embodiment, as described above, the tape-like seal 12 corresponding to the circumferentially innermost one of the plurality of turns of the tape-like seal 12 circumferentially wound on the outer circumferential side of the introduction-side flow path 41 includes the through-hole 12a that overlaps the introduction-side flow path 41 as viewed in the radial direction, and the tape-like seal 14 corresponding to the circumferentially innermost one of the plurality of turns of the tape-like seal 14 circumferentially wound on the outer circumferential side of the discharge-side flow path 51 includes the through-hole 14a that overlaps the discharge-side flow path 51 as viewed in the radial direction. According to this structure, the air accumulated in the introduction-side flow path 41 and the discharge-side flow path 51 can be discharged through the through-hole 12a and the through-hole 14a.

Second Embodiment

The structure of a cell culture apparatus 300 according to a second embodiment is now described with reference to FIGS. 2, 10, and 11. The cell culture apparatus 300 according to the second embodiment blocks the flow of a culture solution with a gasket 63, unlike the structure of the cell culture apparatus 100 according to the first embodiment that blocks the flow of the culture solution with the tape-like seal 12. The same structures as those of the first embodiment are denoted by the same reference numerals, and description thereof is omitted.

(Structure of Cell Culture Apparatus)

Figure 10:
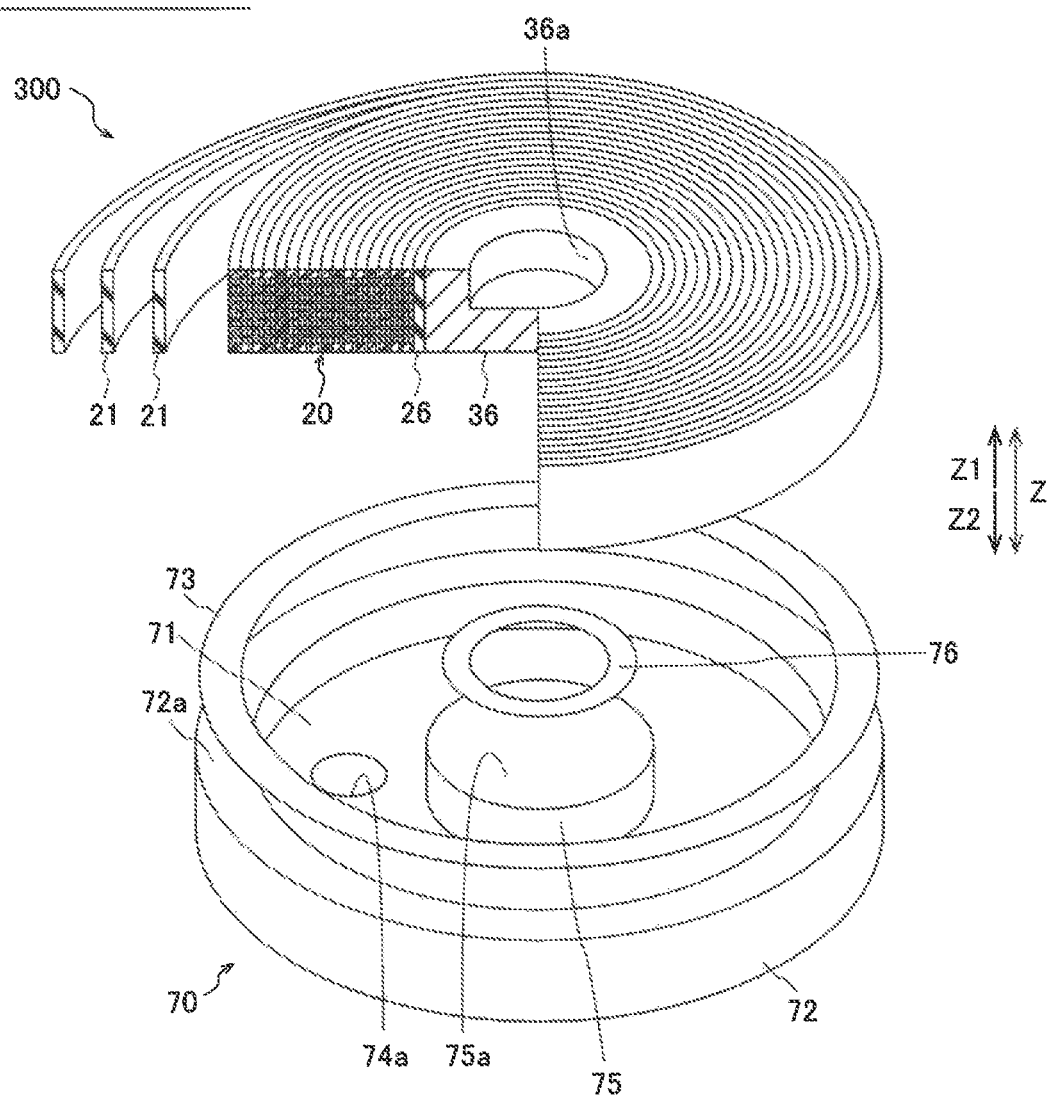
FIG. 10 is a perspective view showing the structure of a cell culture apparatus according to a second embodiment.

As shown in FIG. 10, the cell culture apparatus 300 includes a tape 20 provided with concave wells 2 (see FIG. 2). The cell culture apparatus 300 further includes a blank tape 21 connected to the tape 20. The blank tape 21 is flexible and circumferentially windable on the outer circumferential side of the tape 20 circumferentially wound. Note that the concave wells 2 are not provided on the blank tape 21. The tape 20 and the blank tape 21 are examples of a "flexible strip" and an "outer circumferential side member" in the claims, respectively. In FIG. 10, illustration of an introduction-side housing 60 described below is omitted for simplification.

The cell culture apparatus 300 further includes a blank tape 26 connected to the tape 20. The blank tape 26 is flexible and circumferentially wound on the inner circumferential side of the tape 20 circumferentially wound. The concave wells 2 are not provided on the circumferential surface of the blank tape 26. The blank tape 26 is an example of an "inner circumferential side band" in the claims.

The cell culture apparatus 300 further includes a core 36 around which the tape 20, the blank tape 21, and the blank tape 26 are wound. The core 36 includes a recess 36a on the first side (Z1 direction side) in a direction in which a central axis α extends. The core 36 and the recess 36a are examples of a "second core" and a "third recess" in the claims, respectively.

Figure 11:
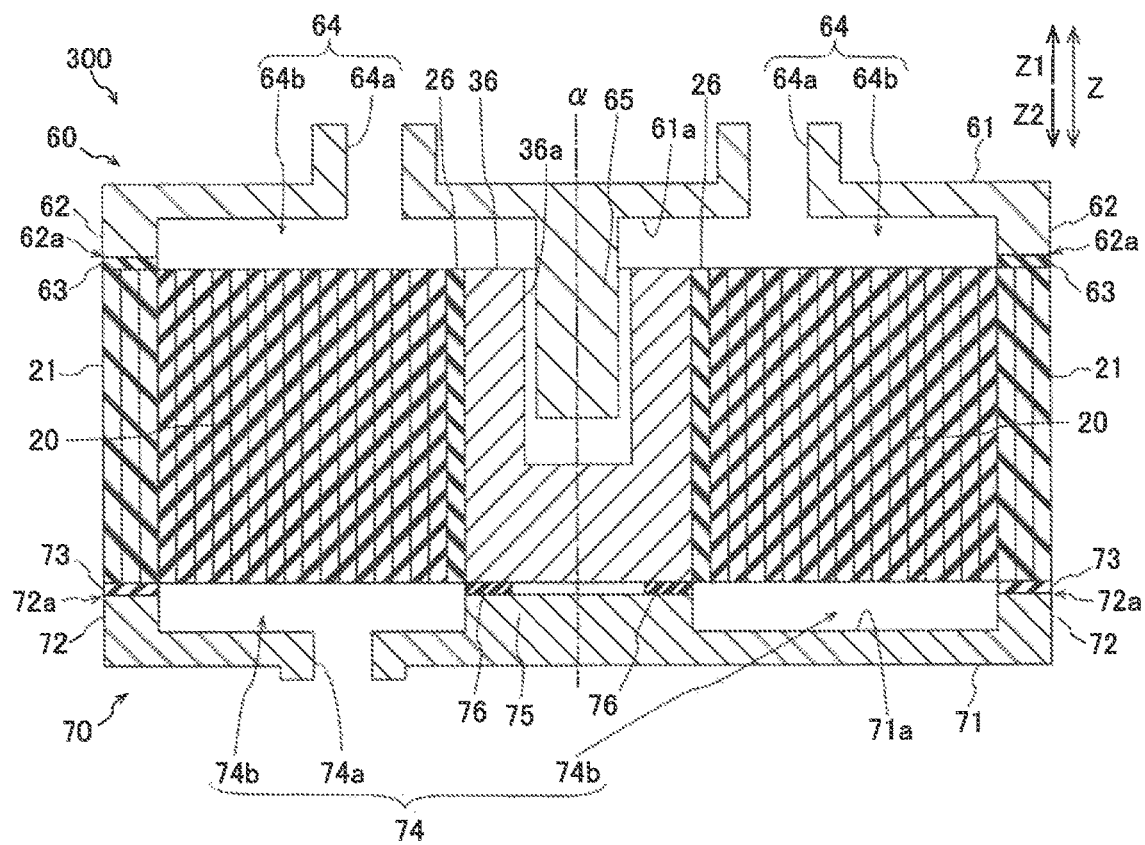
FIG. 11 is a sectional view illustrating the overall structure of the cell culture apparatus according to the second embodiment.

As shown in FIG. 11, the cell culture apparatus 300 further includes the introduction-side housing 60. The introduction-side housing 60 includes an introduction-side main body 61 having a substantially disc shape. The introduction-side housing 60 further includes a protrusion 62 that has a substantially annular shape and protrudes from a surface 61a of the introduction-side main body 61 on the blank tape 21 side (Z2 direction side) toward the blank tape 21 in the direction in which the central axis α extends. The gasket 63 is provided at an end 62a of the protrusion 62 on the blank tape 21 side (Z2 direction side). The protrusion 62 and the gasket 63 are examples of a "second introduction-side protrusion" and a "first introduction-side seal" in the claims, respectively.

In the second embodiment, the cell culture apparatus 300 further includes an introduction unit 64. Specifically, the introduction unit 64 includes an introduction port 64a into which the culture solution is introduced from the outside. The cell culture apparatus 300 further includes an introduction-side flow path 64b through which the culture solution introduced through the introduction port 64a flows. The introduction unit 64 includes the introduction-side flow path 64b.

The gasket 63 blocks the flow of the culture solution from the introduction-side flow path 64b to the outer circumferential side of the tape 20. Specifically, as viewed from the Z1 direction side, the introduction-side flow path 64b is surrounded by the gasket 63.

In a state in which the gasket 63 provided on the protrusion 62 is in close contact with the blank tape 21, the introduction-side flow path 64b is surrounded by the introduction-side main body 61, the protrusion 62, the gasket 63, and the wound tape 20. Specifically, the introduction-side main body 61 covers the introduction-side flow path 64b from the Z1 direction side. Furthermore, the introduction-side flow path 64b is surrounded by the protrusion 62 as viewed from the Z1 direction side.

The gasket 63 entirely covers the blank tape 21 from the Z1 direction side. The gasket 63 may partially cover the blank tape 21 from the Z1 direction side (may cover only a half of the blank tape 21 from the inner circumferential side, for example). In addition, the gasket 63 does not overlap the tape 20 as viewed from the Z1 direction side.

In the second embodiment, the culture solution introduced through the introduction port 64a is introduced into the introduction-side flow path 64b from the first side (Z1 direction side) in the direction in which the central axis α extends. Specifically, the introduction port 64a is provided in the introduction-side main body 61 provided on the Z1 direction side of the introduction-side flow path 64b. The introduction-side flow path 64b communicates with the outside through the introduction port 64a. Two introduction ports 64a are provided at bilaterally symmetrical positions with respect to the central axis α in the introduction-side main body 61.

The introduction-side housing 60 includes a protrusion 65 fitted into the recess 36a of the core 36. Specifically, the protrusion 65 protrudes from the surface 61a of the introduction-side housing 60 toward the Z2 direction side. Moreover, the protrusion 65 has a substantially cylindrical shape. The protrusion 65 is an example of a "third introduction-side protrusion" in the claims.

The cell culture apparatus 300 includes a discharge-side housing 70. The discharge-side housing 70 includes a discharge-side main body 71 having a substantially disc shape (see FIG. 10). The discharge-side housing 70 further includes a protrusion 72 that has a substantially annular shape and protrudes from a surface 71a of the discharge-side main body 71 on the blank tape 21 side (Z1 direction side) toward the blank tape 21 in the direction in which the central axis α extends. A gasket 73 is provided at an end 72a of the protrusion 72 on the blank tape 21 side (Z2 direction side). The protrusion 72 and the gasket 73 are examples of a "second discharge-side protrusion" and a "third discharge-side seal" in the claims, respectively.

The gasket 73 is provided on the outer circumferential side with respect to a discharge-side flow path 74b described below in a state in which the tape 20 is circumferentially wound, and blocks the flow of the culture solution from the discharge-side flow path 74b to the outer circumferential side of the tape 20. Specifically, as viewed from the Z2 direction side, the discharge-side flow path 74b is surrounded by the gasket 73.

In the second embodiment, the cell culture apparatus 300 includes a discharge unit 74. Specifically, the discharge unit 74 includes a discharge port 74a through which the culture solution is outwardly discharged. The cell culture apparatus 300 further includes the discharge-side flow path 74b provided on the second side (Z2 direction side) of the tape 20 in the direction in which the central axis α extends in a state in which the tape 20 is circumferentially wound. The discharge unit 74 includes the discharge-side flow path 74b. The culture solution to be outwardly discharged through the discharge port 74a flows through the discharge-side flow path 74b. The discharge-side flow path 74b is an example of a "second discharge-side flow path" in the claims.

In a state in which the gasket 73 provided on the protrusion 72 is in close contact with the blank tape 21, the discharge-side flow path 74b is surrounded by the discharge-side main body 71, the protrusion 72, the gasket 73, and the wound tape 20. Specifically, the discharge-side main body 71 covers the discharge-side flow path 74b from the Z2 direction side. Furthermore, the discharge-side flow path 74b is surrounded by the gasket 73 and the protrusion 72 as viewed from the Z2 direction side.

The gasket 73 entirely covers the blank tape 21 from the Z2 direction side. The gasket 73 may partially cover the blank tape 21 from the Z2 direction side (may cover only a half of the blank tape 21 from the inner circumferential side, for example). In addition, the gasket 73 does not overlap the tape 20 as viewed from the Z2 direction side.

The discharge port 74a is provided in the discharge-side main body 71. The discharge-side flow path 74b communicates with the outside through the discharge port 74a. Although it is illustrated that only one discharge port 74a is provided in the discharge-side main body 71, two or more discharge ports 74a may be provided.

The discharge-side housing 70 includes a protrusion 75 that protrudes from the surface 71a toward the core 36. The protrusion 75 has a cylindrical shape (see FIG. 10). A gasket 76 having a substantially annular shape (see FIG. 10) is provided on an end surface 75a (see FIG. 10) of the protrusion 75 on the Z2 direction side. The gasket 76 is provided along the outer circumferential edge of the end surface 75a of the protrusion 75. The gasket 76 is sandwiched between the core 36 and the protrusion 75.

The introduction-side flow path 64b and the discharge-side flow path 74b are configured as described above such that it is not necessary to directly connect a surrounding member (such as a pump that supplies the culture solution) to the tape 20 in order to introduce and discharge the culture solution. Thus, the operation such as winding (unwinding) of the tape 20 can be facilitated.

The remaining structures of the second embodiment are similar to those of the aforementioned first embodiment.

Advantages Derived from Second Embodiment

According to the second embodiment, the following advantages are obtained.

According to the second embodiment, as described above, in the cell culture apparatus 300, the introduction-side flow path 64b is surrounded by the introduction-side main body 61, the protrusion 62, the gasket 63, and the wound tape 20 in a state in which the gasket 63 provided on the protrusion 62 is in close contact with the blank tape 21. Accordingly, in a state in which the gasket 63 is in close contact with the blank tape 21, the protrusion 62 and the gasket 63 can significantly reduce or prevent leakage of the culture solution that flows through the introduction-side flow path 64b to the outer circumferential side. Furthermore, in a state in which the gasket 63 is in close contact with the blank tape 21, the introduction-side main body 61 can significantly reduce or prevent leakage of the culture solution that flows through the introduction-side flow path 64b from the first side in the direction in which the central axis α extends.

According to the second embodiment, as described above, the cell culture apparatus 300 includes the gasket 73 provided on the outer circumferential side with respect to the discharge-side flow path 74b in a state in which the tape 20 is circumferentially wound and that blocks the flow of the culture solution from the discharge-side flow path 74b to the outer circumferential side of the tape 20. Furthermore, the cell culture apparatus 300 includes the discharge-side housing 70 including the discharge-side main body 71 having a substantially disc shape and the protrusion 72 having a substantially annular shape, protruding from the surface 71a of the discharge-side main body 71 on the blank tape 21 side toward the blank tape 21 in the direction in which the central axis α extends, and provided with the gasket 73 at the end 72a on the blank tape 21 side. Accordingly, the gasket 73 significantly reduces or prevents leakage of the culture solution from the discharge-side flow path 74b to the outer circumferential side of the tape 20, and thus the culture solution from the discharge-side flow path 74b can more efficiently flow to the discharge port 74a. Furthermore, the gasket 73 is provided at the end 72a of the protrusion 72 on the blank tape 21 side, and thus the gasket 73 can be easily brought into close contact with the blank tape 21.

According to the second embodiment, as described above, in the cell culture apparatus 300, the discharge-side flow path 74b is surrounded by the discharge-side main body 71, the protrusion 72, the gasket 73, and the wound tape 20 in a state in which the gasket 73 provided on the protrusion 72 is in close contact with the blank tape 21. Accordingly, in a state in which the gasket 73 is in close contact with the blank tape 21, the protrusion 72 and the gasket 73 can significantly reduce or prevent leakage of the culture solution that flows through the discharge-side flow path 74b to the outer circumferential side. Furthermore, in a state in which the gasket 73 is in close contact with the blank tape 21, the discharge-side main body 71 can significantly reduce or prevent leakage of the culture solution that flows through the discharge-side flow path 74b from the second side in the direction in which the central axis α extends.

According to the second embodiment, as described above, in the cell culture apparatus 300, the introduction-side housing 60 includes the protrusion 65 fitted into the recess 36a of the core 36. Accordingly, in a state in which the protrusion 65 is fitted into the recess 36a of the core 36, the culture solution can be introduced to culture the cells 101. Consequently, the cells 101 can be cultured while the cell culture apparatus 300 is stably fixed.

According to the second embodiment, as described above, in the cell culture apparatus 300, the culture solution introduced through the introduction port 64a is introduced into the introduction-side flow path 64b from the first side in the direction in which the central axis α extends. The introduction-side flow path 64b is provided on the first side of the tape 20, and thus the culture solution is introduced from the first side of the introduction-side flow path 64b such that the culture solution can be linearly introduced from the instruction port 64a to the tape 20. Consequently, the structure on the introduction side of the culture solution can be relatively simplified.

Description of advantages similar to those obtained in the aforementioned first embodiment among the advantages of the second embodiment is omitted.

Third Embodiment

The structure of a cell culture apparatus 400 according to a third embodiment is now described with reference to FIGS. 3, 5, and 12 to 19. The cell culture apparatus 400 according to the third embodiment includes a housing 80 that does not include a protrusion that protrudes inward, unlike the first embodiment in which the culture solution is introduced and discharged through the protrusion 100c and the protrusion 100e that protrude toward the core 6. The same structures as those of the first embodiment are denoted by the same reference numerals, and description thereof is omitted.

(Structure of Cell Culture Apparatus)

Figure 12:
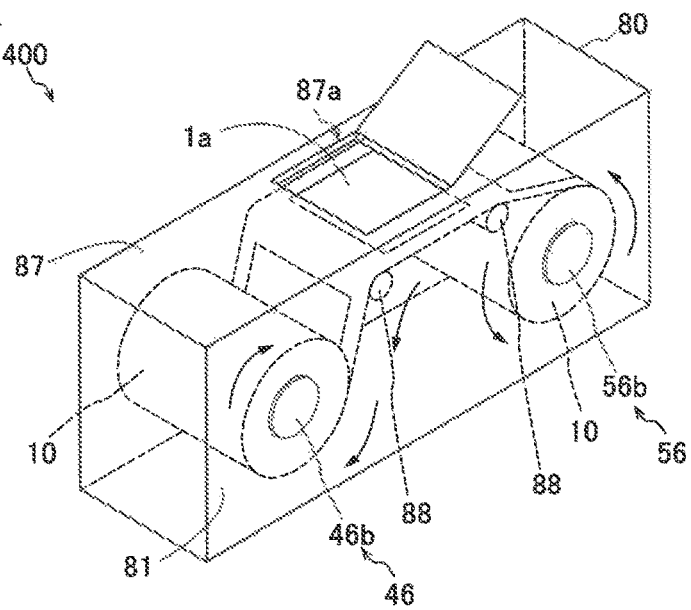
FIG. 12 is a perspective view of a cell culture apparatus according to a third embodiment.

As shown in FIG. 12, the cell culture apparatus 400 includes the housing 80. The housing 80 has a substantially rectangular parallelepiped shape. The housing 80 is made of a resin, for example. Note that in FIG. 12 and FIGS. 17 to 19 described below, illustration of protrusions 81c described below is omitted for simplification.

The housing 80 houses a tape 10. Furthermore, the housing 80 houses at least a portion of a core 46. Specifically, the housing 80 houses a core main body 46a (see FIG. 13) of the core 46. The core main body 46a indicates a portion of the core 46 other than a protruding end 46b and a protruding end 46c (see FIG. 13) described below. The core 46 is an example of a "first core" in the claims.

The housing 80 houses a core main body 56a (see FIG. 13) of a core 56. The core main body 56a indicates a portion of the core 56 other than a protruding end 56b and a protruding end 56c (see FIG. 13) described below. The central axis α1 (see FIG. 13) of the core 46 and the central axis α2 (see FIG. 13) of the core 56 extend substantially parallel to each other.

Figure 13:
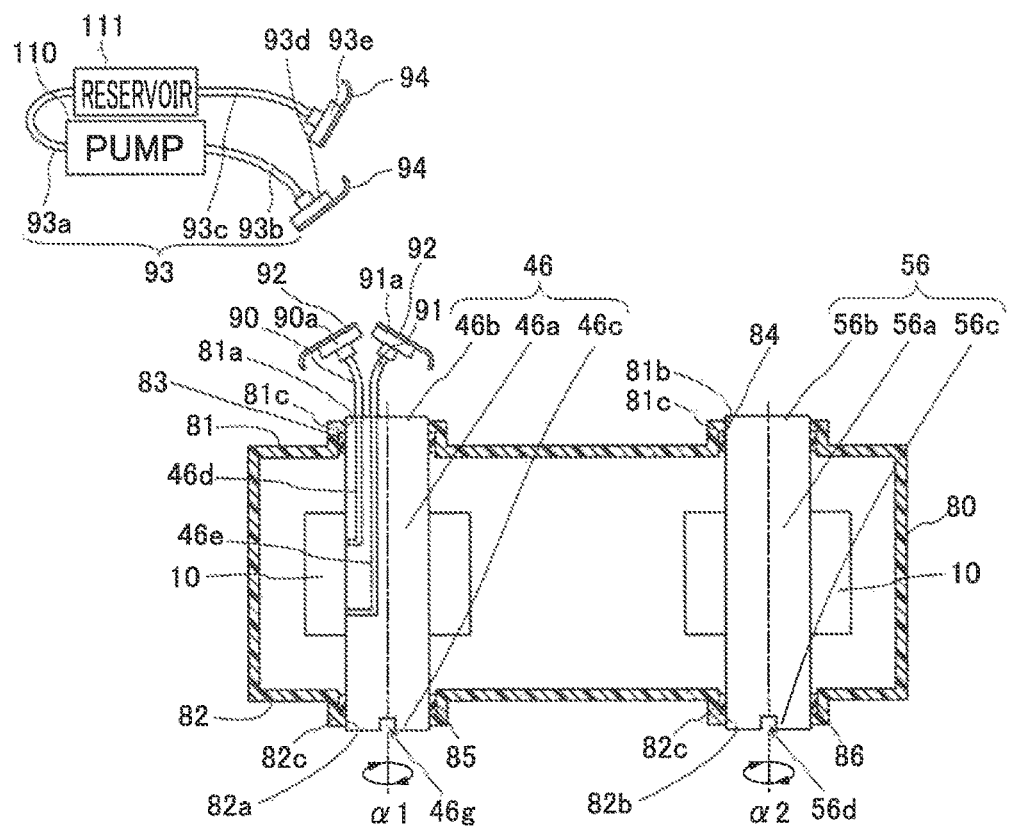
FIG. 13 is a sectional view at the time of tape winding of the cell culture apparatus according to the third embodiment.
Figure 14:
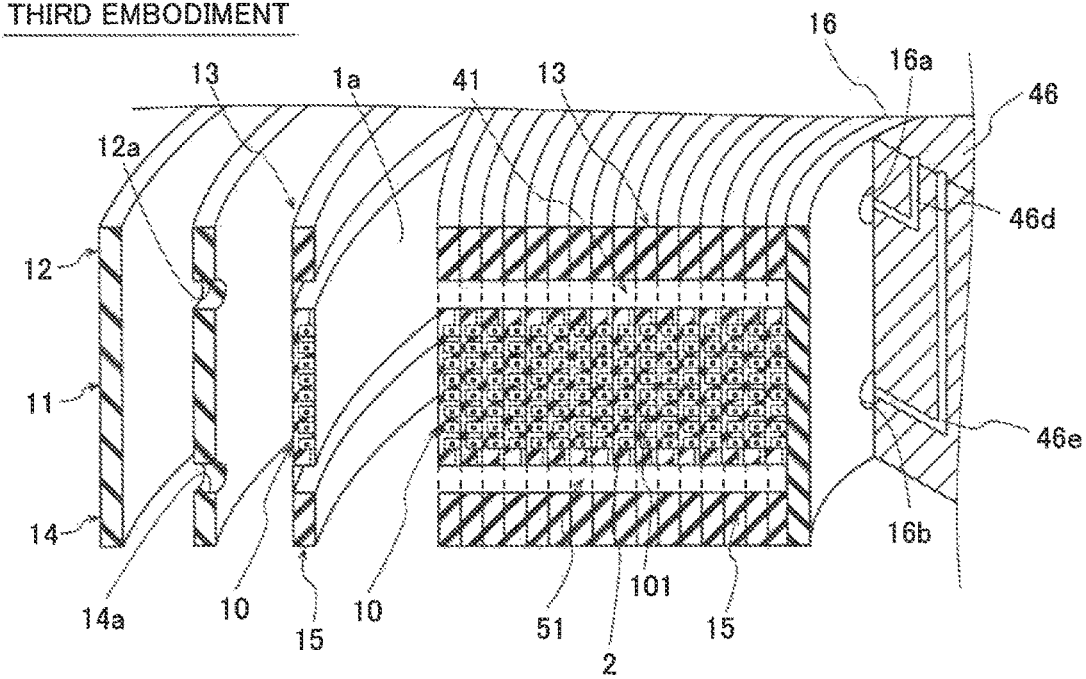
FIG. 14 is a partial sectional view showing the structure of the cell culture apparatus according to the third embodiment.

As shown in FIG. 13, the housing 80 includes an opening 81a and an opening 81b provided in its side surface 81 in a direction in which the central axis α1 (α2) extends. In addition, the housing 80 includes the protrusions 81c that protrude to the outside (the upper side in FIG. 13) of the housing 80. Two protrusions 81c are provided on the side surface 81. The opening 81a is disposed in one of the two protrusions 81c, and the opening 81b is disposed in the other of the two protrusions 81c. The protrusions 81c are an example of a "housing-side protrusion" in the claims.

The housing 80 also includes an opening 82a and an opening 82b provided in its side surface 82 in the direction in which the central axis α1 (α2) extends. In addition, the housing 80 includes protrusions 82c that protrude to the outside (the lower side in FIG. 13) of the housing 80. Two protrusions 82c are provided on the side surface 82. The opening 82a is disposed in one of the two protrusions 82c, and the opening 82b is disposed in the other of the two protrusions 82c. The side surface 81 and the side surface 82 face each other.

The core 46 includes the protruding end 46b provided on one end side of the core 46 in the direction in which the central axis α1 extends. The core 46 also includes the protruding end 46c provided on the other end side of the core 46 in the direction in which the central axis α1 extends. The protruding end 46b protrudes to the outside of the housing 80 through the opening 81a of the housing 80. The protruding end 46c protrudes to the outside of the housing 80 through the opening 82a of the housing 80.

The core 56 includes the protruding end 56b provided on one end side of the core 56 in the direction in which the central axis α2 extends. The core 56 also includes the protruding end 56c provided on the other end side of the core 56 in the direction in which the central axis α2 extends. The protruding end 56b protrudes to the outside of the housing 80 through the opening 81b of the housing 80. Furthermore, the protruding end 56c protrudes to the outside of the housing 80 through the opening 82b of the housing 80.

The core 46 includes a flow path 46d. The flow path 46d extends inside the core 46 from a through-hole 16a (see FIG. 14) to the protruding end 46b of the core 46. The core 46 also includes a flow path 46e. The flow path 46e extends inside the core 46 from a through-hole 16b (see FIG. 14) to the protruding end 46b of the core 46. Each of the flow path 46d and the flow path 46e extends in a substantially L shape. The flow path 46d and the flow path 46e are examples of a "first flow path" and a "second flow path" in the claims, respectively.

Both the flow path 46d and the flow path 46e are provided on one side with respect to the central axis α1 on the cross-section of the core 46. The flow path 46d and the flow path 46e may sandwich the central axis α1 on the cross-section of the core 46. Also, one of the flow path 46d and the flow path 46e may extend toward the protruding end 46c.

The cell culture apparatus 400 further includes a tube 90 connected to the flow path 46d of the protruding end 46b of the core 46. The tube 90 is connected to the flow path 46d so as to allow a culture solution to flow into the flow path 46d. The cell culture apparatus 400 further includes a tube 91 connected to the flow path 46e of the protruding end 46b of the core 46. The tube 91 is connected to the flow path 46e such that the culture solution from the flow path 46e flows into the tube 91. That is, the tube 90 and the tube 91 are respectively connected to the flow path 46d and the flow path 46e outside the housing 80.

The cell culture apparatus 400 further includes a sterile connector 90a that separates and connects a first-side portion 93b of a tube 93 described below and the tube 90. The cell culture apparatus 400 further includes a sterile connector 91a that separates and connects a second-side portion 93c of the tube 93 described below and the tube 91. Specifically, the sterile connector 90a is provided at an end of the tube 90 opposite to the flow path 46d. The sterile connector 91a is provided at an end of the tube 91 opposite to the flow path 46e. Each of the sterile connectors 90a and 91a is attached with a cap 92 that prevents contamination of bacteria, for example, when the sterile connectors 90a and 91a are separated from the tube 93 described below. The sterile connector 90a and the sterile connector 91a are examples of a "first joint" and a "second joint" in the claims, respectively.

The cell culture apparatus 400 further includes a pump 110 that delivers the culture solution. Moreover, the cell culture apparatus 400 includes a reservoir 111 that stores the culture solution.

The cell culture apparatus 400 further includes the tube 93. The tube 93 includes an intermediate portion 93a that connects the pump 110 to the reservoir 111. The tube 93 also includes the first-side portion 93b that extends from the pump 110. The tube 93 also includes the second-side portion 93c that extends from the reservoir 111. The tube 93 is an example of a "third tube" in the claims.

The cell culture apparatus 400 further includes a sterile connector 93d that separates and connects the first-side portion 93b of the tube 93 and the tube 90. The cell culture apparatus 400 further includes a sterile connector 93e that separates and connects the second-side portion 93c of the tube 93 and the tube 91. Specifically, the sterile connector 93d is provided at an end of the first-side portion 93b of the tube 93 opposite to the pump 110. The sterile connector 93e is provided at an end of the second-side portion 93c of the tube 93 opposite to the reservoir 111. Each of the sterile connectors 93d and 93e is attached with a cap 94 that prevents contamination of bacteria, for example, when the sterile connectors 93d and 93e are separated from the tubes 90 and 91. The sterile connector 93d and the sterile connector 93e are examples of a "first joint" and a "second joint" in the claims, respectively.

Figure 15:
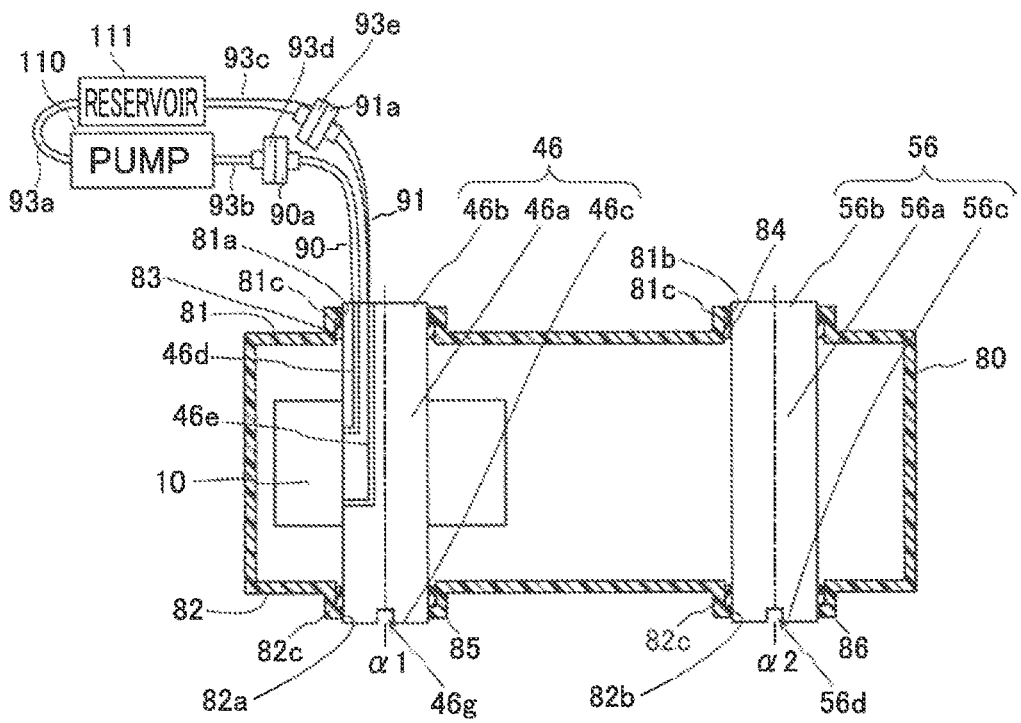
FIG. 15 is a sectional view at the time of culture solution introduction of the cell culture apparatus according to the third embodiment.

That is, the sterile connector 90a of the tube 90 and the sterile connector 93d of the first-side portion 93b of the tube 93 are separated from each other and connected to each other such that the tube 90 and the tube 93 (first-side portion 93b) are separated from each other and connected to each other (see FIG. 15). In addition, the sterile connector 91a of the tube 91 and the sterile connector 93e of the second-side portion 93c of the tube 93 are separated from each other and connected to each other such that the tube 91 and the tube 93 (second-side portion 93c) are separated from each other and connected to each other (see FIG. 15). By using the sterile connector 90a (sterile connector 93d) and the sterile connector 91a (sterile connector 93e), it is possible to connect and separate the tubes 90 and 91 and the tube 93 while maintaining airtightness.

In the third embodiment, the cell culture apparatus 400 includes an annular O-ring 83 disposed adjacent to the opening 81a of the housing 80 and that circumferentially surrounds the core 46. Specifically, as the core 46 rotates, the outer circumferential surface 46f (see FIG. 16) of the core 46 slides on the inner circumferential surface 83a (see FIG. 16) of the O-ring 83. The inner circumferential surface 83a of the O-ring 83 is smooth such that the core 46 can easily rotate. The O-ring 83 is made of a resin, for example. The O-ring 83 is an example of a "sealing member" in the claims.

Figure 16:
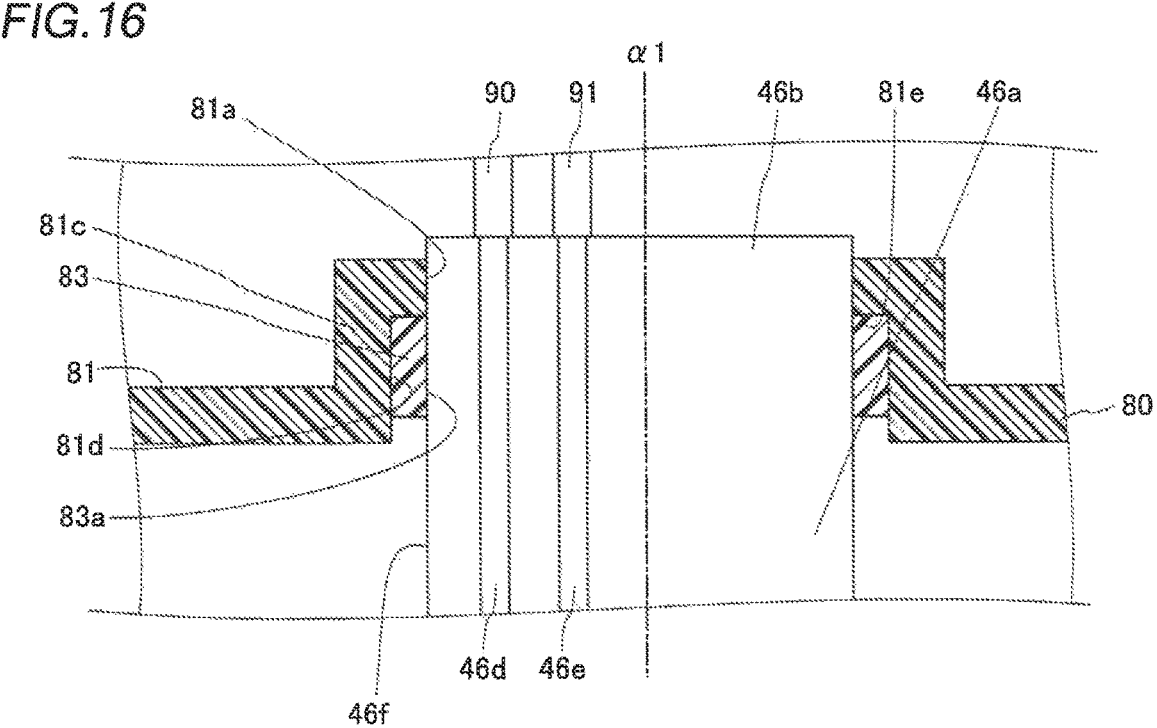
FIG. 16 is a partial enlarged view of the vicinity of a protruding end in FIG. 13.

As shown in FIG. 16, the O-ring 83 is sandwiched between the inner circumferential surface 81d of the protrusion 81c and the outer circumferential surface 46f of the core 46 inside the housing 80. Furthermore, the O-ring 83 comes into contact with the end surface 81e of the protrusion 81c on the opening 81a side inside the housing 80.

The cell culture apparatus 400 further includes an O-ring 84 (see FIG. 15) disposed adjacent to the opening 81b of the housing 80, an O-ring 85 (see FIG. 15) disposed adjacent to the opening 82a, and an O-ring 86 (see FIG. 15) disposed adjacent to the opening 82b. The structures and arrangements of the O-rings 84 to 86 are similar to those of the O-ring 83, and thus detailed description thereof is omitted.

As shown in FIG. 12, the housing 80 includes a window 87a provided in a side surface 87 that extends along the direction in which the central axis α1 (α2) (see FIG. 13) extends. The window 87a is openable and closable. When the window 87a is closed, the inside of the housing 80 is sealed (airtightness is maintained). The window 87a has a substantially rectangular shape. The window 87a may have a shape (a circular shape, for example) other than the rectangular shape.

Inside the housing 80, two guides 88 are provided between the core 46 and the core 56. The core 46 and the core 56 rotate while the tape 10 is guided by the two guides 88 such that the tape 10 wound around the core 46 is wound around the core 56 (or the tape 10 wound around the core 56 is wound around the core 46). The protruding end 46c of the core 46 is provided with a groove 46g to which a jig (such as a driver) (not shown) that rotates the core 46 is attached. Furthermore, the protruding end 56c of the core 56 is provided with a groove 56d to which a jig (such as a driver) (not shown) that rotates the core 56 is attached. The core 46 (56) is rotated by rotating the jig with a motor or the like such that the tape 10 can be wound around the core 46 (56). The motors that respectively drive the core 46 and the core 56 are simultaneously driven. Furthermore, the groove 56d may be provided at the protruding end 56b.

When the tape 10 is wound around the core 46 or the core 56 while being guided by the guides 88, the tape 10 is moved along the window 87a in a state in which the inner circumferential surface 1a of the tape 10 faces the window 87a. That is, in such a case, the window 87a and the inner circumferential surface 1a of the tape 10 overlap each other as viewed in a direction perpendicular to the side surface 87.

A method for using the cell culture apparatus 400 is now described with reference to FIGS. 17 to 19.

Figure 17:
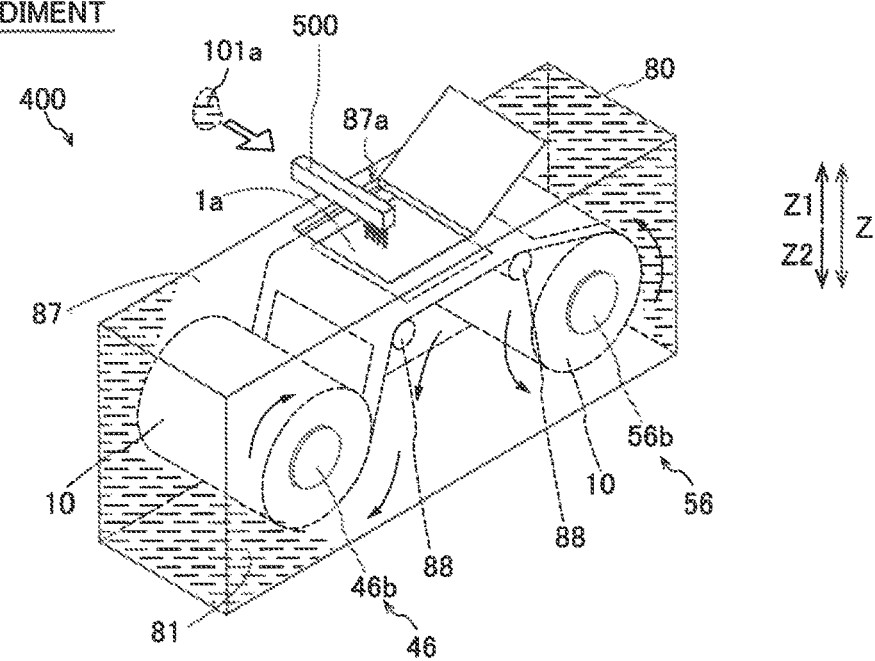
FIG. 17 is a perspective view at the time of cell seeding (introduction) of the cell culture apparatus according to the third embodiment.

As shown in FIG. 17, when the tape 10 wound around the core 56 is wound around the core 46 in a state in which the window 87a is open, a cell suspension 101a including cells 101 is introduced into the housing 80 by a cell seeding apparatus 500 (an ink jet, for example) through the window 87a. Consequently, the cells 101 are seeded in wells 2 (see FIG. 3) provided on the inner circumferential surface 1a of the tape 10 that moves along the window 87a. Although illustration is omitted, in this step, the tube 90 (see FIG. 13) and the tube 91 (see FIG. 13) are connected to the core 46, but the tubes 90 and 91 are not connected to the tube 93 (see FIG. 13). Furthermore, the cell suspension 101a flows into the housing 80 in a state in which the side surface 87 of the housing 80 faces upward (in a Z1 direction in FIG. 17). In this step, the inside of the housing 80 is filled with the culture solution, for example.

Figure 18:
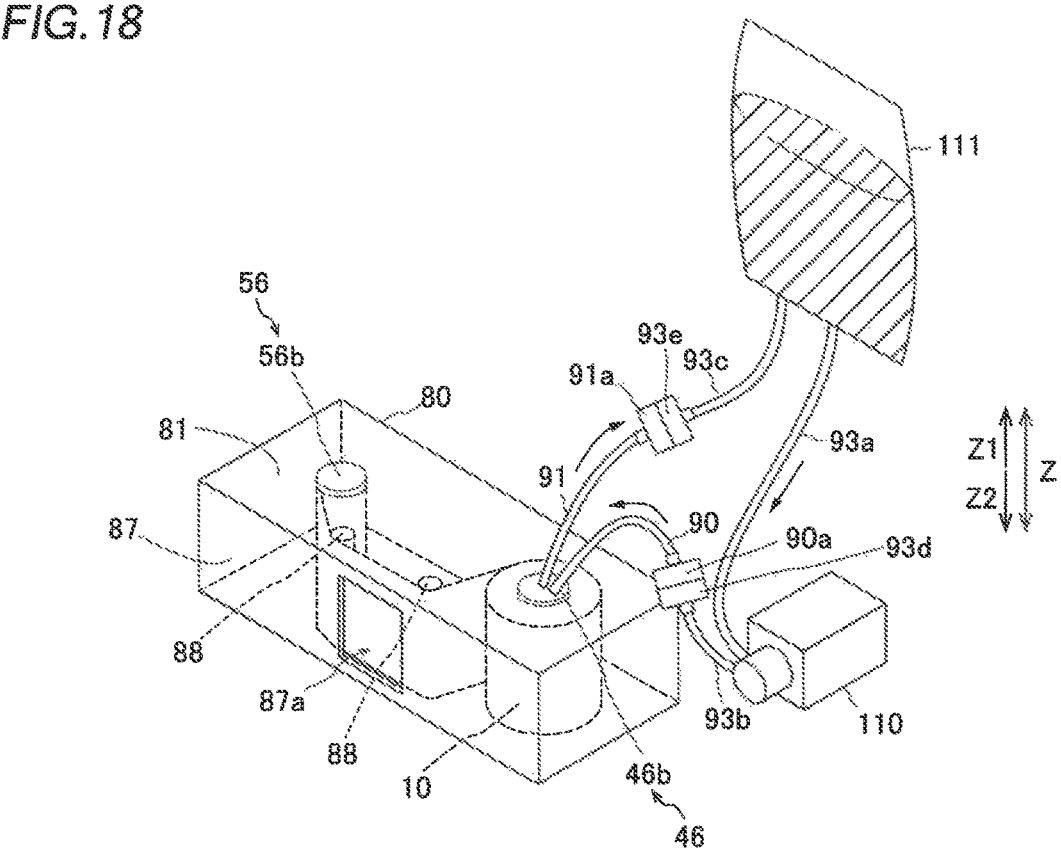
FIG. 18 is a perspective view at the time of culture solution introduction of the cell culture apparatus according to the third embodiment.

Next, as shown in FIG. 18, substantially the entire tape 10 is wound around the core 46, and then the culture solution is introduced into the flow path 46d (see FIG. 13) of the core 46 through the tube 90. In such a case, the tube 90 and the first-side portion 93b of the tube 93 (see FIG. 13) are connected to each other, and the tube 91 and the second-side portion 93c of the tube 93 are connected to each other.

Then, the culture solution is drawn from the flow path 46e (see FIG. 13) of the core 46 through the tube 91. The culture solution drawn from the flow path 46e of the core 46 is stored in the reservoir 111. Then, the culture solution stored in the reservoir 111 is again delivered to the flow path 46e of the core 46 by the pump 110. In this step, the culture solution is introduced in a state in which the protruding end 46b of the core 46 faces upward (in the Z1 direction in FIG. 18). In this step, the window 87a is closed. Furthermore, in this step, the culture solution in the housing 80 is discharged, and the inside of the housing 80 is filled with air. The culture solution in the housing 80 is discharged from the window 87a or a discharge port (not shown).

Figure 19:
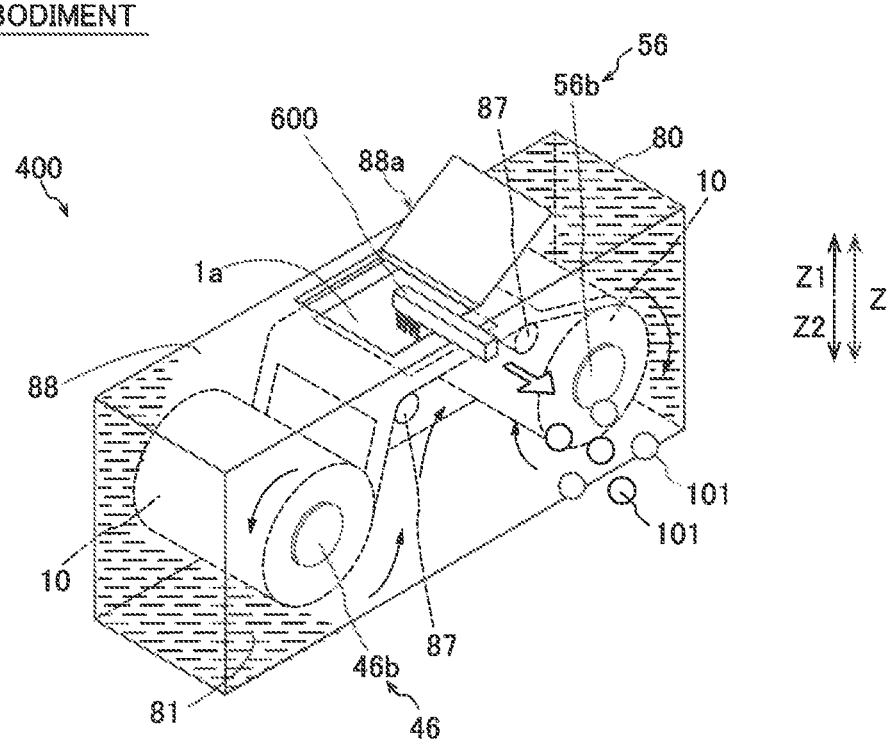
FIG. 19 is a perspective view at the time of cell collection of the cell culture apparatus according to the third embodiment.

Next, as shown in FIG. 19, the tape 10 wound around the core 46 is wound around the core 56 in a state in which the window 87a is open. At this time, the cells 101 seeded in the wells 2 (see FIG. 3) are collected by a cell collection device 600 (a suction nozzle, for example) through the window 87a. Although illustration is omitted, in this step, the tube 90 (see FIG. 13) and the tube 91 (see FIG. 13) are connected to the core 46, but the tube 90 and the tube 91 are not connected to the tube 93 (FIG. 13). In addition, the cells 101 are collected in a state in which the side surface 87 of the housing 80 faces upward (in the Z1 direction in FIG. 19). In this step, the inside of the housing 80 is filled with the culture solution, for example.

Advantages Derived from Third Embodiment

According to the third embodiment, the following advantages are obtained.

According to the third embodiment, as described above, the core 46 includes the protruding end 46b provided on at least one end side of the core 46 in the direction in which the central axis α1 extends and that protrudes to the outside of the housing 80 through the opening 81a of the housing 80. Furthermore, the cell culture apparatus 400 includes the tube 90 connected to the flow path 46d of the protruding end 46b of the core 46 and through which the culture solution flows into the flow path 46d, and the tube 91 connected to the flow path 46e of the protruding end 46b of the core 46 and into which the culture solution flows from the flow path 46e. In addition, the cell culture apparatus 400 includes the annular O-ring 83 disposed adjacent to the opening 81a of the housing 80 and that circumferentially surrounds the core 46. When the tube 90 and the tube 91 are inserted into the inside of the housing 80, the inserted portions of the tube 90 and the tube 91 are conceivably fixed by a sealing member, for example, in order to maintain the sealability of the inside of the housing 80. In such a case, when the core 46 is rotated in a state in which the tube 90 and the tube 91 are inserted into the inside of the housing 80, the tube 90 and the tube 91 may be twisted with the inserted portions of the tube 90 and the tube 91 into the housing 80 as fulcrums. On the other hand, when the tube 90 and the tube 91 are respectively connected to the flow path 46d and the flow path 46e of the protruding end 46b that protrudes to the outside of the housing 80, it is not necessary to insert the tube 90 and the tube 91 into the inside of the housing 80. Accordingly, when the core 46 is rotated, twisting of the tube 90 and the tube 91 can be significantly reduced or prevented. Furthermore, the annular O ring 83 is provided adjacent to the opening 81a of the housing 80 such that even when the protruding end 46b of the core 46 protrudes to the outside of the housing 80, the sealability of the housing 80 can be maintained by the annular O-ring 83. Consequently, twisting of the tube 90 and the tube 91 can be significantly reduced or prevented while the sealability of the housing 80 is maintained.

According to the third embodiment, as described above, in the cell culture apparatus 400, the O-ring 83 is sandwiched between the inner circumferential surface 81d of the protrusion 81c and the outer circumferential surface 46f of the core 46 inside the housing 80. Accordingly, the O-ring 83 is sandwiched between the inner circumferential surface 81d of the protrusion 81c and the outer circumferential surface 46f of the core 46 such that the O-ring 83 can be stably disposed. Consequently, the core 46 can be rotated while the sealability of the housing 80 is more effectively maintained by the O-ring 83.

According to the third embodiment, as described above, the cell culture apparatus 400 includes the sterile connectors (90a, 93d) that separate and connect the first-side portion 93b of the tube 93 and the tube 90, and the sterile connectors (91a, 93e) that separate and connect the second-side portion 93c of the tube 93 and the tube 91. Accordingly, the sterile connectors (90a, 93d) and the sterile connectors (91a, 93e) are provided such that when the core 46 is rotated, the tube 93 can be separated from the tube 90 and the tube 91 in each of the sterile connectors (90a, 93d) and the sterile connectors (91a, 93e). Consequently, when the core 46 is rotated, twisting of the tube 90 and the tube 91 can be further significantly reduced or prevented.

Description of advantages similar to those obtained in the aforementioned first embodiment among the advantages of the third embodiment is omitted.

Modified Examples

The embodiments disclosed this time must be considered as illustrative in all points and not restrictive. The scope of the present invention is not shown by the above description of the embodiments but by the scope of claims for patent, and all modifications (modified examples) within the meaning and scope equivalent to the scope of claims for patent are further included.

For example, while the culture solution is introduced from the inner circumferential side into the introduction-side flow path 41 in each of the aforementioned first and third embodiments, the present invention is not limited to this. For example, the culture solution may alternatively be introduced from the outer circumferential side into the introduction-side flow path 41.

While the upper housing 100a and the lower housing 100b are separately provided in the aforementioned first embodiment, the present invention is not limited to this. For example, the upper housing 100a and the lower housing 100b may alternatively be integrally provided.

While the introduction-side housing 60 and the discharge-side housing 70 are separately provided in the aforementioned second embodiment, the present invention is not limited to this. For example, the introduction-side housing 60 and the discharge-side housing 70 may alternatively be integrally provided.

While the wells 2 and the culture solution flow paths 3 are provided on the inner circumferential surface 1a of the tape (10, 20) (flexible strip) in each of the aforementioned first to third embodiments, the present invention is not limited to this. For example, the wells 2 and the culture solution flow paths 3 may alternatively be provided on the outer circumferential surface 1b of the tape (10, 20) (flexible strip).

While the blank tape (11, 21) (outer circumferential side member) is provided in each of the aforementioned first to third embodiments, the present invention is not limited to this. For example, the blank tape (11, 21) (outer circumferential side member) may not be provided. Alternatively, the blank tape (16, 26) (inner circumferential side band) may not be provided.

While the two introduction ports 40 are provided in the aforementioned first embodiment, the present invention is not limited to this. For example, only one introduction port 40 may alternatively be provided, and one introduction port 40 may alternatively be connected to the two flow paths 100d (third flow path). Furthermore, only one discharge port 50 may alternatively be provided, and one discharge port 50 may alternatively be connected to the two flow paths 100f (fourth flow path).

While each of the flow path 6c (first flow path) and the flow path 6d (second flow path) extends in the radial direction in the aforementioned first embodiment, the present invention is not limited to this. For example, the flow path 6c (first flow path) may alternatively be inclined downward toward the outer diameter side, and the flow path 6d (second flow path) may alternatively be inclined downward toward the inner diameter side.

While each of the through-hole 16a (third through-hole) and the through-hole 16b (fourth through-hole) extends in the radial direction in each of the aforementioned first and third embodiments, the present invention is not limited to this. For example, the through-hole 16a (third through-hole) may alternatively be inclined downward toward the outer diameter side, and the through-hole 16b (fourth through-hole) may alternatively be inclined downward toward the inner diameter side.

While each of the introduction-side flow path 41 and the discharge-side flow path 51 (first discharge-side flow path) extends in the radial direction on the cross-section in the radial direction in each of the aforementioned first and third embodiments, the present invention is not limited to this. For example, the introduction-side flow path 41 may alternatively be inclined downward toward the outer diameter side, and the discharge-side flow path 51 (first discharge-side flow path) may alternatively be inclined downward toward the inner diameter side.

While the gasket 7 (second introduction-side seal) is provided on the first side in the direction in which the central axis α extends with respect to the portion in which the culture solution flows from the flow path 100d (third flow path) into the flow path 6c (first flow path) in the aforementioned first embodiment, the present invention is not limited to this. For example, the gasket sandwiched between the protrusion 100c (first introduction-side protrusion) and the core 6 (first core) may alternatively be provided also on the second side in the direction in which the central axis α extends with respect to the portion in which the culture solution flows from the flow path 100d (third flow path) into the flow path 6c (first flow path). In addition, the gasket sandwiched between the protrusion 100e (first discharge-side protrusion) and the core 6 (first core) may alternatively be provided also on the first side in the direction in which the central axis α extends with respect to the portion in which the culture solution flows from the flow path 6d (second flow path) into the flow path 100f (fourth flow path).

While the blank tape 11 (21) (outer circumferential side member) has a flexible band (tape) shape in each of the aforementioned first to third embodiments, the present invention is not limited to this. For example, a rigid member such as a resin member or a metal member may alternatively be provided on the outer circumferential side of the tape 10 (20) (flexible strip).

While both ends of the core 46 (first core) protrude from the housing 80 in the aforementioned third embodiment, the present invention is not limited to this. For example, only one end of the core 46 (first core) may alternatively protrude from the housing 80. Similarly, only one end of the core 56 may alternatively protrude from the housing 80, or both ends of the core 56 may not protrude from the housing 80.

While the O-ring 83 (sealing member) is provided on the inner side of the protrusion 81c (housing-side protrusion) of the housing 80 in the aforementioned third embodiment, the present invention is not limited to this. For example, the O-ring 83 (sealing member) may alternatively be provided on the inner circumferential side of the opening 81a of the housing 80.

While the tube 90 (first tube) and the tube 91 (second tube) are separated from the tube 93 (third tube) when the tape 10 (flexible strip) is wound in the aforementioned third embodiment, the present invention is not limited to this. In a state in which the tube 90 (first tube) and the tube 91 (second tube) are connected to the tube 93 (third tube), the tape 10 (flexible strip) may alternatively be wound.

While one flow path 46d (first flow path) for introducing the culture solution and one flow path 46e (second flow path) for discharging the culture solution are provided in the aforementioned third embodiment, the present invention is not limited to this. A plurality of flow paths 46d (first flow paths) and a plurality of flow paths 46e (second flow paths) may alternatively be provided. In such a case, a plurality of tubes 90 (first tubes) and a plurality of tubes 91 (second tubes) are also provided.

What is claimed is:
1. A cell culture apparatus comprising:
a base layer that is flexible and circumferentially windable and having thereon a flexible strip that is windable and provided with a plurality of concave wells for culturing cells therein, the flexible base layer disposed proximate the concave wells in a radial direction when the flexible culturing strip and flexible base layer are wound;

an introduction-side flow path provided on a first side of the flexible culturing strip in an axial direction from the concave wells when the flexible culturing strip and base layer are circumferentially wound, the introduction-side flow path being arranged to allow a culture solution introduced to flow therethrough and be introduced into the plurality of concave wells of the flexible culturing strip when circumferentially wound; and the flexible base layer having a flexible first introduction-side seal thereon and wound on an outer circumferential side of the flexible culturing strip in the radial direction when circumferentially wound, the first introduction-side seal being configured to block flow of the culture solution from the introduction-side flow path past the outer circumferential side of the flexible culturing strip.

2. The cell culture apparatus according to claim 1, wherein
the flexible culturing strip includes a culture solution flow path connected to the plurality of concave wells, the culture solution flow path being arranged to allow the culture solution to flow therethrough; and
the introduction-side flow path being connected to the culture solution flow path such that culture solution can flow from the introduction side flow path to the plurality of concave wells.

3. The cell culture apparatus according to claim 1, wherein the base layer includes an outer circumferential side member connected to the flexible culturing strip and provided on the outer circumferential side of the flexible culturing strip circumferentially wound; and
the first introduction-side seal is connected to a portion of the outer circumferential side member on the first side in the direction in which the central axis extends in the state in which the flexible culturing strip is circumferentially wound.

4. The cell culture apparatus according to claim 3, wherein
the outer circumferential side member is flexible and circumferentially windable with the flexible culturing strip and base layer;
the first introduction-side seal is flexible and integrally provided on the portion of the outer circumferential side member on the first side; and
the outer circumferential side member is circumferentially wound around an outer circumference of the flexible culturing strip such that the first introduction-side seal is circumferentially wound on the outer circumferential side of the introduction-side flow path.

5. The cell culture apparatus according to claim 4, further comprising a first-side band provided on the base layer of the flexible culturing strip in an axial direction from the introduction side flow path, the first-side band having a band shape so as to be circumferentially windable together with the flexible culturing strip and base layer and capable of blocking flow of culture solution in an axial direction such that the culture solution enters the concave wells; wherein
the introduction-side flow path comprises a first-side groove provided between the flexible culturing strip and the first-side band in a state in which the flexible culturing strip, the flexible base layer and the first-side band are integrally wound, and a plurality of first through-holes that extend from the first-side groove in one wind to the first-side groove in an adjacent wind.

6. The cell culture apparatus according to claim 4, wherein the culture solution introduced is introduced from an inner radial side of the introduction-side flow path into the introduction-side flow path.

7. The cell culture apparatus according to claim 4, further comprising:
a first discharge-side flow path provided on a second side of the flexible culturing strip in an axial direction opposite from the first introduction-side flow path when the flexible culturing strip and base layer are circumferentially wound, the first discharge-side flow path being arranged to allow the culture solution to flow from the concave wells to be discharged radially inwardly; and
the base layer having a first discharge-side seal provided on an outer circumferential side of the first discharge-side flow path in a radial direction in the state in which the flexible culturing strip and base layer are circumferentially wound, the first discharge-side seal being configured to block flow of the culture solution from the first discharge-side flow path past the outer circumferential side of the flexible culturing strip and base layer; wherein
the first discharge-side seal is flexible and integrally provided on the outer circumferential side member; and
the outer circumferential side member is circumferentially wound around the outer circumference of the flexible culturing strip such that the first discharge-side seal is circumferentially wound on the outer circumferential side of the first discharge-side flow path.

8. The cell culture apparatus according to claim 7, wherein the base layer has a second-side band thereon integrally provided on the second axial side of the flexible culturing strip, the second-side band having a band shape so as to be circumferentially windable together with the flexible culturing strip and base layer and prevents culture fluid from exiting in an axial direction and is capable of directing culture fluid in a direction towards an inner core of the wound tape; and
the first discharge-side flow path includes a second-side groove provided between the flexible culturing strip and the second-side band in a state in which the flexible culturing strip and the second-side band are integrally wound, and a plurality of second through-holes that extend from the second-side groove in one wind to the second-side groove in an adjacent wind.

9. The cell culture apparatus according to claim 7,
the base layer having an inner side band connected to the flexible culturing strip, the inner side band being flexible and is circumferentially wound on an inner radial side of the flexible culturing strip circumferentially wound; and
a first core arranged to allow the flexible culturing strip, flexible base layer and the inner circumferential side band to be wound therearound; wherein
the inner circumferential side band includes a third through-hole arranged to allow the culture solution introduced to flow therethrough into the introduction-side flow path in a state in which the flexible culturing strip and the inner circumferential side band are wound, and a fourth through-hole arranged to allow the culture solution to flow thereinto from the first discharge-side flow path; and
the first core includes a first flow path arranged to allow the culture solution introduced to flow therethrough into the third through-hole of the inner circumferential side band, and a second flow path arranged to allow the culture solution to flow thereinto through the fourth through-hole of the inner circumferential side band.

10. The cell culture apparatus according to claim 9, further comprising:
a first introduction-side protrusion fitted into a first recess provided in the first core on the first side in the direction in which the central axis extends, the first introduction-side protrusion including a third flow path arranged to allow the culture solution introduced to flow therethrough into the first flow path of the first core; and
a second introduction-side seal sandwiched between the first introduction-side protrusion and the first core on the first side in the direction in which the central axis extends with respect to a portion arranged to allow the culture solution to flow therethrough from the third flow path into the first flow path.

11. The cell culture apparatus according to claim 9, further comprising:
a first discharge-side protrusion fitted into a second recess provided in the first core on the second side in the direction in which the central axis extends, the first discharge-side protrusion including a fourth flow path arranged to allow the culture solution to flow thereinto from the second flow path of the first core; and
a second discharge-side seal sandwiched between the first discharge-side protrusion and the first core on the second side in the direction in which the central axis extends with respect to a portion arranged to allow the culture solution to flow therethrough from the second flow path into the fourth flow path.

12. The cell culture apparatus according to claim 7, wherein
the first introduction-side seal corresponding to circumferentially innermost one of a plurality of turns of the first introduction-side seal circumferentially wound on the outer circumferential side of the introduction-side flow path includes a fifth through-hole that overlaps the introduction-side flow path as viewed in a radial direction; and
the first discharge-side seal corresponding to circumferentially innermost one of a plurality of turns of the first discharge-side seal circumferentially wound on the outer circumferential side of the first discharge-side flow path includes a sixth through-hole that overlaps the first discharge-side flow path as viewed in the radial direction.

13. The cell culture apparatus according to claim 9, further comprising a housing configured to house the flexible culturing strip and at least a portion of the first core; wherein
the housing includes an opening provided in a side surface in the direction in which the central axis extends;
the first core includes a protruding end provided on at least one end side of the first core in the direction in which the central axis extends, the protruding end protruding to an outside of the housing through the opening of the housing; and
the cell culture apparatus further comprises:

a first tube connected to the first flow path of the protruding end of the first core, the first tube being arranged to allow the culture solution to flow therethrough into the first flow path;
a second tube connected to the second flow path of the protruding end of the first core, the second tube being arranged to allow the culture solution to flow thereinto from the second flow path; and
an annular sealing member disposed adjacent to the opening of the housing, the annular sealing member circumferentially surrounding the first core.

14. The cell culture apparatus according to claim 13, wherein
the housing includes a housing-side protrusion in which the opening is disposed, the housing-side protrusion protruding to the outside of the housing; and
the sealing member is sandwiched between an inner circumferential surface of the housing-side protrusion and an outer circumferential surface of the first core inside the housing.

15. The cell culture apparatus according to claim 13, further comprising:
a pump configured to deliver the culture solution;
a reservoir configured to store the culture solution;
a third tube including an intermediate portion that connects the pump to the reservoir, a first-side portion that extends from the pump, and a second-side portion that extends from the reservoir;
a first joint that separates and connects the first-side portion of the third tube and the first tube; and
a second joint that separates and connects the second-side portion of the third tube and the second tube.

16. The cell culture apparatus according to claim 1, wherein the flexible culturing strip consists of a single layer.

17. The cell culture apparatus according to claim 7, wherein the introduction side flow path and the discharge side flow path are grooves disposed on the base layer when it is unwound, and when wound, form disc-shaped channels that allow culture solution to enter and exit, and wherein the grooves are positioned such that culture solution is capable of passing into the disc shaped introduction side flow path, and via the plurality of concave wells to the disc shaped discharge side flow path.

18. The cell culture apparatus according to claim 17, wherein the first side band and second side band are bands on the base layer and when wound, form first and second side discs that are capable of blocking culture medium from flowing out axially.

19. The cell culture apparatus according to claim 18, wherein openings to the introduction and discharge side flow paths are capable of allowing culture medium to enter from a central core when the culture apparatus is wound, passing radially outwardly through the introduction flow path, then axially via the concave wells towards the discharge fluid flow path, and passes radially inwardly via the discharge flow path back to exit at the central core of the wound cell culture apparatus.

* * * * *